United States Patent [19]

Haaf et al.

[11] Patent Number: 5,714,436
[45] Date of Patent: Feb. 3, 1998

[54] N-HETEROARYL-N'-(PYRID-2-YLSULFONYL)UREAS, PROCESSES FOR THEIR PREPARATION, AND THEIR USE AS HERBICIDES AND PLANT GROWTH REGULATORS

[75] Inventors: Klaus Haaf, Kelkheim; Heinz Kehne, Hofheim; Klaus Bauer, Hanau; Hermann Bieringer, Eppstein, all of Germany

[73] Assignee: Hoechst Schering AgrEvo GmbH, Berlin, Germany

[21] Appl. No.: 592,393

[22] PCT Filed: Aug. 8, 1994

[86] PCT No.: PCT/EP94/02628

§ 371 Date: Mar. 22, 1996

§ 102(e) Date: Mar. 22, 1996

[87] PCT Pub. No.: WO95/06049

PCT Pub. Date: Mar. 2, 1995

[30] Foreign Application Priority Data

Aug. 24, 1993 [DE] Germany .......................... 43 28 397.7
Oct. 19, 1993 [DE] Germany .......................... 43 35 587.0

[51] Int. Cl.$^6$ ..................... C07D 521/00; A01N 47/36
[52] U.S. Cl. .......................... 504/211; 504/213; 504/215; 504/216; 544/212; 544/298; 544/320; 544/331; 546/272.4; 546/293
[58] Field of Search ................. 504/211, 213, 504/215, 216; 544/212, 218, 219, 180, 298, 307, 315, 320, 335, 278, 253, 331; 546/272.4, 293

[56] References Cited

U.S. PATENT DOCUMENTS

| | | | |
|---|---|---|---|
| 4,421,550 | 12/1983 | Selby et al. | 504/211 |
| 4,487,626 | 12/1984 | Zimmerman | 504/215 |
| 4,579,583 | 2/1989 | Föry et al. | 504/215 |
| 4,662,933 | 5/1987 | Thompson | 504/215 |
| 5,221,315 | 6/1993 | Föry et al. | 504/178 |
| 5,529,976 | 6/1996 | Kehne et al. | 504/213 |

FOREIGN PATENT DOCUMENTS

| | | |
|---|---|---|
| 0 013 480 | 7/1980 | European Pat. Off. . |
| 0 084 224 | 7/1983 | European Pat. Off. . |
| 0 103 543 | 3/1984 | European Pat. Off. . |
| 0 125 864 | 11/1984 | European Pat. Off. . |
| 0 272 855 | 6/1988 | European Pat. Off. . |
| 314505 | 5/1989 | European Pat. Off. . |
| WO 88/04297 | 6/1988 | WIPO . |
| WO 91/10660 | 7/1991 | WIPO . |

Primary Examiner—Bernard Dentz
Assistant Examiner—Lyman H. Smith
Attorney, Agent, or Firm—Curtis, Morris & Safford, P.C.

[57] ABSTRACT

Compounds of the formula (I) or salts thereof

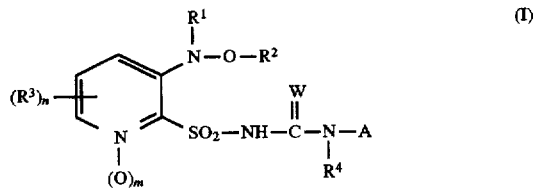

in which $R^1$-$R^4$, W, A, n and m are as defined in claim 1, for example $R^1$ and $R^2$ are H, (substituted) alkyl, (substituted) alkenyl or alkynyl, (substituted) cycloalkyl, (substituted) aryl or acyl and A is (substituted) pyrimidinyl or triazinyl are suitable as selective sulfonylurea herbicides and plant growth regulators.

(I) is prepared analogously to known processes via intermediates, some of which are novel, for example via suitably substituted pyridylsulfonamides (II) and N-tert-butylsulfonamides (VIII) as claimed in claim 5.

9 Claims, No Drawings

N-HETEROARYL-N'-(PYRID-2-YLSULFONYL)UREAS, PROCESSES FOR THEIR PREPARATION, AND THEIR USE AS HERBICIDES AND PLANT GROWTH REGULATORS

This application is a 35 U.S.C. 371 National Stage filing of PCT EP/94/02628 published as WO95/06049 on Mar. 2, 1995.

The invention relates to the technical field of herbicides and plant growth regulators, in particular of herbicides for the selective control of broad-leaved weeds and grass weeds in crops of useful plants.

It has been disclosed that some 2-pyridylsulfonyl ureas have herbicidal and plant growth-regulating properties; cf. EP-A-13 480, EP-A-272 855, EP-A-84224, U.S. Pat. No. 4,421,550, EP-A-103543 (U.S. Pat. No. 4,579,583) U.S. Pat. No. 4,487,626, EP-A-125864, WO 88/04297 and WO 91/10660 (ZA 91/0173).

Further 2-pyridylsulfonyl ureas which have specific radicals in the 3-position of the pyridyl radical and which are suitable as herbicides and plant growth regulators have now been found.

The present invention relates to compounds of the formula (I) or to salts thereof,

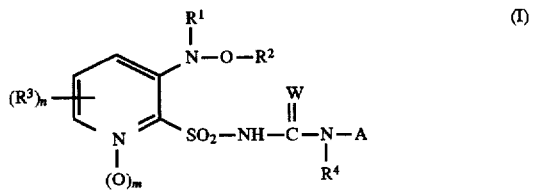

in which $R^1$ is H, $(C_1-C_6)$alkyl which is unsubstituted or substituted by one or more radicals selected from the group consisting of halogen, nitro, $(C_1-C_4)$alkoxy, $(C_3-C_6)$cycloalkyl, cyano, aryl and substituted aryl, $(C_3-C_6)$cycloalkyl which is unsubstituted or substituted by one or more radicals selected from the group consisting of halogen, $(C_1-C_4)$alkyl and $(C_1-C_4)$alkoxy, or $(C_2-C_6)$alkenyl or $(C_2-C_6)$alkynyl, each of the two last-mentioned radicals being unsubstituted or substituted by one or more radicals selected from the group consisting of halogen, $(C_1-C_4)$alkoxy and $(C_3-C_6)$cycloalkyl, or is aryl, substituted aryl, or an acyl radical of the formula

—CO—R* in which

R* is H, $(C_1-C_6)$alkyl, $(C_2-C_6)$alkenyl or $(C_2-C_6)$alkynyl, each of the three last-mentioned radicals being unsubstituted or substituted by one or more radicals selected from the group consisting of halogen, $(C_1-C_4)$alkoxy, $(C_1-C_4)$alkylthio, $(C_1-C_4)$alkylsulfinyl, $(C_1-C_4)$alkylsulfonyl, nitro, cyano, thiocyanato, aryl, and substituted aryl, or is $(C_1-C_4)$alkoxy, $(C_2-C_4)$alkenyloxy, $(C_2-C_4)$alkynyloxy or $(C_1-C_4)$alkylthio, each of the last-mentioned four radicals being unsubstituted or substituted by one or more radicals selected from the group consisting of halogen, $(C_1-C_4)$alkoxy, $(C_1-C_4)$alkylthio, aryl and substituted aryl, or is $(C_3-C_6)$cycloalkyl or $(C_3-C_6)$cycloalkoxy, each of the last-mentioned two radicals being unsubstituted or substituted by one or more radicals selected from the group consisting of $(C_1-C_4)$alkyl, $(C_1-C_4)$alkoxy, $(C_1-C_4)$alkylthio, $(C_1-C_4)$haloalkyl, and halogen, or is a radical of the formula $NR^aR^b$, $R^2$ is H, $(C_1-C_6)$alkyl which is unsubstituted or substituted by one or more radicals selected from the group consisting of halogen, nitro, $(C_1-C_4)$alkoxy, $(C_3-C_6)$cycloalkyl, aryl and substituted aryl, or $(C_3-C_6)$cycloalkyl which is unsubstituted or substituted by one or more radicals selected from the group consisting of halogen, $(C_1-C_4)$alkyl, $(C_1-C_4)$alkoxy, $(C_1-C_4)$haloalkyl, aryl and substituted aryl, or $(C_2-C_6)$alkenyl or $(C_2-C_6)$alkynyl, each of the last-mentioned two radicals being unsubstituted or substituted by one or more radicals selected from the group consisting of $(C_1-C_4)$alkoxy, $(C_1-C_4)$haloalkyl, $(C_3-C_6)$cycloalkyl and halogen, or aryl, substituted aryl or a radical of the formula $R'R''R'''Si$, in which R', R" and R'" independently of one another are $(C_1-C_4)$alkyl, or an acyl radical of the formula

—CO—R** in which

R** is H, $(C_1-C_6)$alkyl, $(C_2-C_6)$alkenyl or $(C_2-C_6)$alkynyl, each of the three last-mentioned radicals being unsubstituted or substituted by one or more radicals selected from the group consisting of halogen, $(C_1-C_4)$alkoxy, $(C_1-C_4)$alkylthio, $(C_1-C_4)$alkylsulfinyl, $(C_1-C_4)$alkylsulfonyl, nitro, cyano, thiocyanato, aryl, and substituted aryl, or is $(C_1-C_4)$alkoxy, $(C_2-C_4)$alkenyloxy or $(C_2-C_4)$alkynyloxy, each of the last-mentioned three radicals being unsubstituted or substituted by one or more radicals selected from the group consisting of halogen, $(C_1-C_4)$alkoxy, $(C_1-C_4)$alkylthio, aryl and substituted aryl, or is $(C_3-C_6)$cycloalkyl or $(C_3-C_6)$cycloalkoxy, each of the last-mentioned two radicals being unsubstituted or substituted by one or more radicals selected from the group consisting of halogen, $(C_1-C_4)$alkyl, $(C_1-C_4)$alkoxy, $(C_1-C_4)$alkylthio and $(C_1-C_4)$haloalkyl, or is a radical of the formula $NR^cR^d$, $R^3$ is $(C_1-C_4)$alkyl, $(C_1-C_3)$haloalkyl, halogen, $NO_2$, CN, $(C_1-C_3)$alkoxy, $(C_1-C_3)$haloalkoxy, $(C_1-C_3)$alkylthio, $(C_1-C_3)$alkoxy-$(C_1-C_3)$alkyl, [$(C_1-C_3)$alkoxy]-carbonyl, $(C_1-C_3)$alkylamino, di[$(C_1-C_3)$alkyl]-amino, $(C_1-C_3)$alkylsulfinyl, $(C_1-C_3)$alkylsulfonyl, $SO_2NR^eR^f$ or $C(O)NR^gR^h$, $R^a$, $R^b$, $R^c$, $R^d$, $R^e$, $R^f$, $R^g$ and $R^h$ independently of one another are H, $(C_1-C_4)$alkyl, $(C_3-C_6)$alkenyl, $(C_3-C_6)$alkynyl, [$(C_1-C_4)$alkyl]-carbonyl, arylcarbonyl which is substituted in the aryl radical or substituted by one or more radicals selected from the group consisting of halogen, $(C_1-C_4)$alkyl and $(C_1-C_4)$alkoxy, or the pairs $R^a$ and $R^b$, $R^c$ and $R^d$, $R^e$ and $R^f$ or $R^g$ and $R^h$ together with the nitrogen atom linking them are a heterocyclic saturated or unsaturated ring having 3 to 7 ring atoms, which can contain, besides the nitrogen atom, 1 or 2 further heteroatoms selected from the group consisting of N, O and S at the oxidation levels which are possible and which is unsubstituted or substituted, $R^4$ is H or $(C_1-C_4)$alkyl, preferably H or $CH_3$, in particular H, m is 0 or 1, preferably 0, n is 0, 1 or 2, preferably 0 or 1, A is a radical of the formula

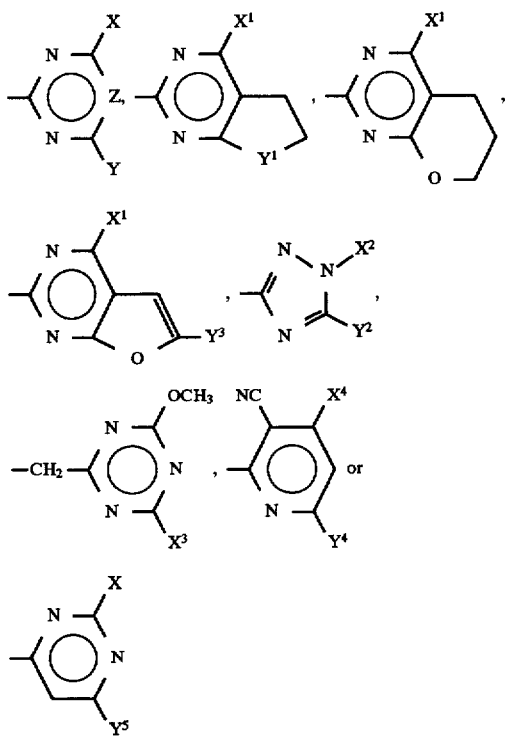

X and Y independently of one another are H, halogen, $(C_1-C_3)$alkyl, $(C_1-C_3)$alkoxy or $(C_1-C_3)$alkylthio, with the abovementioned alkyl-containing radicals being unsubstituted or mono- or polysubstituted by halogen or mono- or disubstituted by $(C_1-C_3)$alkoxy or $(C_1-C_3)$alkylthio, or are a radical of the formula $NR^5R^6$, $(C_3-C_6)$-cycloalkyl, $(C_2-C_4)$alkenyl, $(C_2-C_4)$alkynyl, $(C_3-C_4)$alkenyloxy or $(C_3-C_4)$alkynyloxy, $R^5$ and $R^6$ independently of one another are H, $(C_1-C_3)$alkyl or $(C_3-C_4)$alkenyl, W is O or S, preferably O, Z is CH or N, preferably CH, $X^1$ is $CH_3$, $OCH_3$, $OC_2H_5$ or $OCF_2H$, $Y^1$ is —O— or —$CH_2$—, $X^2$ is $CH_3$, $C_2H_5$ or $CH_2CF_3$, $Y^2$ is $OCH_3$, $OC_2H_5$, $SCH_3$, $SC_2H_5$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl and $Y^5$ is $CH_3$, $C_2H_5$, $OCH_3$ or Cl.

In formula (I) and hereinbelow, hydrocarbon-containing radicals, such as, for example, alkyl, alkoxy, haloalkyl and alkylthio radicals and the corresponding unsaturated and/or substituted radicals can in each case be straight-chain or branched in the hydrocarbon moiety. Alkyl radicals, also in composite meanings, such as alkoxy, haloalkyl and the like, are methyl, ethyl, n- or i-propyl or n-, i-, t- or 2-butyl; alkenyl and alkynyl radicals have the meaning of the unsaturated radicals which are possible and which correspond to the alkyl radicals, such as 2-propenyl, 2- or 3-butenyl, 2-propynyl and 2- or 3-butynyl. Halogen is fluorine, chlorine, bromine or iodine. Haloalkyl is alkyl which is substituted by one or more atoms selected from the halogen group; haloalkyl is, for example, $CF_3$, $CHF_2$, $CH_2CF_3$. Aryl is, for example, phenyl, naphthyl, tetrahydronaphthyl, indanyl, fluorenyl and the like, preferably phenyl. Substituted aryl or substituted phenyl is preferably aryl or phenyl which is substituted by one or more, preferably 1 to 3, radicals selected from the group consisting of halogen, alkyl, haloalkyl, haloalkoxy, nitro, cyano, alkoxycarbonyl, alkanoyl, carbamoyl, mono- and dialkylaminocarbonyl, mono- and dialkylamino, alkylsulfinyl or alkylsulfonyl, those alkyl-containing radicals having 1 to 4 carbon atoms, in particular 1 to 2 carbon atoms, being preferred; particularly preferred are methyl, methoxy and chlorine. Examples of heterocyclic radicals $NR^aR^b$, $NR^cR^d$, $NR^eR^f$ or $NR^gR^h$ are optionally substituted pyrrole, imidazole, pyrazole, triazole, pyrazolone, oxazole, oxazolone, propanesultam, butanesultam, pyrrolidone, piperidine and morpholine. Suitable substituents in substituted heterocyclic radicals are those which have been mentioned for cycloalkyl and aryl radicals, in particular $(C_1-C_4)$alkyl, $(C_1-C_4)$alkoxy, $(C_1-C_4)$haloalkyl, $(C_1-C_4)$haloalkoxy and halogen.

The invention also relates to all stereoisomers which are embraced by formula (I) and to mixtures thereof. Such compounds of the formula (I) contain one or more asymmetric carbon atoms or else double bonds which are not specifically mentioned in the formulae (I). The stereoisomers which are possible and which are defined by their specific spatial shape, such as enantiomers, diastereomers and Z and E isomers, however, are all embraced by the formulae (I) and can be obtained by customary methods from stereoisomer mixtures or else prepared by stereoselective reactions in combination with the use of stereochemically pure starting substances.

The compounds of the formula (I) can form salts in which the hydrogen of the —$SO_2$—NH group is replaced by an agriculturally suitable cation. Examples of these salts are metal salts, in particular alkali metal salts (sodium or potassium salts), or alkaline earth metal salts, or else ammonium salts, or salts with organic amines. Salt formation can equally be effected by an addition reaction of a strong acid with the pyridine moiety of the compound of the formula (I). Acids which are suitable for this purpose are strong inorganic and organic acids, for examples, HCl, HBr, $H_2SO_4$ or $HNO_3$.

Compounds (I) according to the invention which are of particular interest are those in which $R^1$ is H, $(C_1-C_4)$alkyl which is unsubstituted or substituted by one or more radicals selected from the group consisting of halogen, preferably F, Cl and Br, $(C_1-C_4)$alkoxy, $(C_3-C_6)$cycloalkyl or phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy and $(C_1-C_4)$alkylthio, or $(C_3-C_6)$cycloalkyl, $(C_2-C_4)$alkenyl, $(C_2-C_4)$haloalkenyl, $(C_2-C_4)$alkynyl, phenyl, substituted phenyl or a radical of the formula

—CO—R* in which

R* is H, $(C_1-C_4)$alkyl, $(C_2-C_4)$alkenyl or $(C_2-C_4)$alkynyl, each of the three last-mentioned radicals being unsubstituted or substituted by one or more radicals selected from the group consisting of halogen, $(C_1-C_4)$alkoxy, $(C_1-C_4)$alkylsulfonyl, phenyl and substituted phenyl, or is $(C_1-C_4)$alkoxy which is unsubstituted or substituted by one or more radicals selected from the group consisting of halogen, $(C_1-C_4)$alkoxy, $(C_1-C_4)$alkylthio, phenyl and substituted aryl, or $(C_3-C_6)$cycloalkyl or $(C_3-C_6)$cycloalkoxy, each of the lastmentioned two radicals being unsubstituted or substituted by one or more radicals selected from the group consisting of $(C_1-C_4)$alkyl, $(C_1-C_4)$alkoxy and halogen, or is a radical of the formula $NR^aR^b$.

Preferred compounds of the formula (I) according to the invention or salts thereof are those in which $R^1$ is hydrogen or $(C_1-C_4)$alkyl which is unsubstituted or substituted by 1 to 3 radicals selected from the halogen group or by $(C_1-C_2)$ alkoxy or $(C_3-C_5)$cycloalkyl.

Other preferred compounds of the formula (I) according to the invention or salts thereof are those in which $R^1$ is a radical of the formula —CO—$R^*$ in which $R^*$ is hydrogen, $(C_1-C_4)$alkyl which is unsubstituted or substituted by one or more halogen atoms or by $(C_1-C_2)$alkoxy, or $(C_2-C_4)$ alkenyl, $(C_2-C_3)$alkynyl, $(C_3-C_5)$cycloalkyl, $(C_1-C_4)$ alkoxy which is unsubstituted or substituted by one or more halogen atoms or by phenyl, or a radical of the formula $NR^aR^b$, in which $R^a$ and $R^b$ independently of one another are H or $(C_1-C_4)$alkyl.

Other compounds of the formula (I) according to the invention and salts thereof which are of particular interest are those in which $R^2$ is H, $(C_1-C_4)$alkyl which is unsubstituted or substituted by one or more radicals selected from the group consisting of halogen, $(C_1-C_4)$alkoxy, $(C_3-C_6)$ cycloalkyl, phenyl and substituted phenyl, or $(C_3-C_6)$ cycloalkyl which is unsubstituted or substituted by one or more radicals selected from the group consisting of halogen, $(C_1-C_4)$alkyl, $(C_1-C_4)$alkoxy or $(C_1-C_4)$ haloalkyl, or $(C_2-C_4)$alkenyl or $(C_2-C_4)$alkynyl, each of the last-mentioned two radicals being unsubstituted or substituted by one or more radicals selected from the group consisting of $(C_1-C_4)$alkoxy, $(C_1-C_4)$haloalkyl and halogen, or is phenyl, substituted phenyl or a radical of the formula R'R"R'''Si, in which R', R" and R''' independently of one another are $(C_1-C_4)$alkyl, or an acyl radical of the formula

—CO—$R^{}$ in which $R^{}$ is H, $(C_1-C_4)$alkyl, $(C_2-C_4)$alkenyl or $(C_2-C_4)$ alkynyl, each of the three last-mentioned radicals being unsubstituted or substituted by one or more radicals selected from the group consisting of halogen, $(C_1-C_4)$ alkoxy, $(C_1-C_4)$alkylsulfonyl, phenyl and substituted phenyl, or is $(C_1-C_4)$alkoxy, $(C_3-C_4)$alkenyloxy or $(C_3-C_4)$alkynyloxy, each of the last-mentioned three radicals being unsubstituted or substituted by one or more radicals selected from the group consisting of halogen, $(C_1-C_4)$alkoxy, $(C_1-C_4)$alkylthio, phenyl and substituted phenyl, or is $(C_3-C_6)$cycloalkyl or $(C_3-C_6)$ cycloalkoxy, each of the last-mentioned two radicals being unsubstituted or substituted by one or more radicals selected from the group consisting of halogen, $(C_1-C_4)$alkyl, $(C_1-C_4)$alkoxy and $(C_1-C_4)$haloalkyl, or a radical of the formula $NR^cR^d$.

Other preferred compounds of the formula (I) according to the invention and salts thereof are those in which $R^2$ is H, $(C_1-C_4)$alkyl, $(C_1-C_4)$haloalkyl, [$(C_1-C_4)$ alkoxy]-$(C_1-C_4)$alkyl or a radical of the formula —CO—$R^{}$ in which $R^{}$ is H, $(C_1-C_4)$alkyl, $(C_1-C_4)$haloalkyl, $(C_3-C_4)$ alkenyl, $(C_3-C_4)$alkynyl, $(C_1-C_4)$alkoxy, [$(C_1-C_2)$ alkoxy]-$(C_1-C_2)$alkyl, $(C_3-C_5)$cycloalkyl or a radical of the formula $NR^cR^d$ in which $R^c$ and $R^d$ independently of one another are H or $(C_1-C_4)$alkyl.

$R^3$ is preferably $(C_1-C_3)$alkyl, $(C_1-C_3)$haloalkyl, halogen, $NO_2$, $(C_1-C_3)$alkoxy, $(C_1-C_3)$haloalkoxy, $(C_1-C_2)$alkoxy-$(C_1-C_2)$alkyl, acetyl, propionyl, $(C_1-C_2)$alkylamino, di[$(C_1-C_2)$alkyl]-amino, $(C_1-C_3)$ alkylsulfonyl, $SO_2NR^eR^f$ or $C(O)NR^gR^h$.

$R^a$, $R^b$, $R^c$, $R^d$, $R^e$, $R^f$, $R^g$ and $R^h$ independently of one another are preferably H, $(C_1-C_4)$alkyl, allyl, but-2-enyl, but-3-enyl, propargyl, but-2-ynyl, but-3-ynyl, propionyl, acetyl, phenylcarbonyl which is unsubstituted in the phenyl radical or substituted by one or more radicals selected from the group consisting of halogen, $(C_1-C_4)$alkyl and $(C_1-C_4)$ alkoxy, or the pairs $R^a$ and $R^b$, $R^c$ and $R^d$, $R^e$ and $R^f$ or $R^g$ and $R^h$ together with the nitrogen atom linking them are a heterocyclic saturated or unsaturated ring having 5 or 6 ring atoms which can, besides the nitrogen atom, contain one or two further heteroatoms selected from the group consisting of N, O and S at the oxidation levels which are possible and which is unsubstituted or substituted by one or more radicals selected from the group consisting of methyl, ethyl, methoxy, ethoxy, halogen and $(C_1-C_2)$haloalkyl.

Other preferred compounds of the formula (I) according to the invention or salts thereof are those in which $R^3$ is $(C_1-C_4)$alkyl, $(C_1-C_3)$haloalkyl, halogen, $(C_1-C_3)$ alkoxy or nitro and n is 0, 1 or 2, preferably 0 or 1.

Other preferred compounds of the formula (I) or salts thereof are those in which $R^1$ is H, $(C_1-C_4)$alkyl, $(C_1-C_4)$haloalkyl or [$(C_1-C_2)$ alkoxy]-$(C_1-C_2)$alkyl, or a radical of the formula —CO—$R^*$ in which $R^*$ is H, $(C_1-C_4)$alkyl, halo-$(C_1-C_4)$alkyl, $(C_2-C_4)$ alkenyl, $(C_2-C_4)$alkynyl, $(C_1-C_4)$alkoxy, [$(C_1-C_2)$ alkoxy]-$(C_1-C_2)$alkyl, $(C_3-C_5)$cycloalkyl or a radical of the formula $NR^aR^b$ in which $R^a$ and $R^b$ independently of one another are H or $(C_1-C_4)$alkyl.

$R^2$ is H, $(C_1-C_4)$alkyl, $(C_1-C_4)$haloalkyl, [$(C_1-C_2)$ alkoxy]-$(C_1-C_2)$alkyl or a radical of the formula —CO—$R^{}$ in which $R^{}$ is H, $(C_1-C_4)$alkyl, $(C_1-C_4)$haloalkyl, $(C_3-C_4)$ alkenyl, $(C_3-C_4)$alkynyl, $(C_1-C_4)$alkoxy, [$(C_1-C_2)$ alkoxy]-$(C_1-C_2)$alkyl, $(C_3-C_5)$cycloalkyl or a radical of the formula $NR^cR^d$, in which $R^c$ and $R^d$ independently of one another are H or $(C_1-C_4)$alkyl.

$R^3$ is $(C_1-C_4)$alkyl, halogen, nitro or $(C_1-C_4)$alkoxy and n is 0 or 1.

Other preferred compounds of the formula (I) according to the invention or salts thereof are those in which $R^1$ is H, $CH_3$ or $C_2H_5$ and $R^*$ is H, $(C_1-C_4)$alkyl, $(C_1-C_2)$haloalkyl, vinyl, cyclopropyl, cyclobutyl, $(C_1-C_2)$alkoxy or $N(CH_3)_2$, in particular H.

Other preferred compounds of the formula (I) according to the invention or salts thereof are those in which A is a radical of the formula

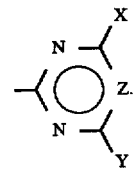

Preferably, one of the radicals X and Y is $(C_1-C_3)$alkyl, $(C_1-C_3)$alkoxy, $(C_1-C_3)$haloalkyl, $(C_1-C_3)$haloalkoxy or [$(C_1-C_2)$alkoxy]-$(C_1-C_2)$alkyl and the other radical Y or X is $(C_1-C_3)$alkyl, $(C_1-C_3)$alkoxy or $(C_1-C_3)$alkylthio, each of the last-mentioned 3 radicals being unsubstituted or monoor polysubstituted by halogen or mono- or disubstituted by $(C_1-C_3)$alkoxy or $(C_1-C_3)$alkylthio, or is halogen or a radical of the formula $NR^5R^6$, in which $R^5$ and $R^6$ independently of one another are H, $(C_1-C_3)$alkyl or $(C_3-C_4)$alkenyl, or $(C_3-C_6)$cycloalkyl, $(C_2-C_4)$alkenyl, $(C_2-C_4)$alkynyl, $(C_3-C_4)$alkenyloxy or $(C_3-C_4)$alkynyloxy.

It is even more preferred for one of the radicals X and Y to be $(C_1-C_2)$alkyl, $(C_1-C_2)$alkoxy or $OCF_2H$ and for the other radical Y or X to be $(C_1-C_2)$alkyl, $(C_1-C_2)$alkoxy, halogen, $OCF_2H$, $OCH_2CF_3$ or $CF_3$.

In particular, X and Y independently of one another are $(C_1-C_2)$alkyl or $(C_1-C_2)$alkoxy.

Also preferred are compounds of the formula (I) according to the invention or salts thereof in which a combination of two or more of the meanings (features) which have been mentioned as being preferred are present.

The invention furthermore relates to processes for the preparation of the compounds of the formula (I) according to the invention or to salts thereof, which comprise a) reacting a compound of the formula (II),

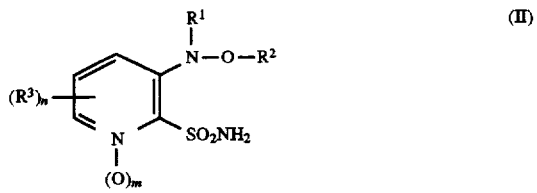

with a heterocyclic carbamate of the formula (III), $$R^o-O-CO-NR^4-A \qquad (III)$$

in which $R^o$ is optionally substituted phenyl or $(C_1-C_4)$alkyl, or b) reacting a pyridylsulfonylcarbamate of the formula (IV),

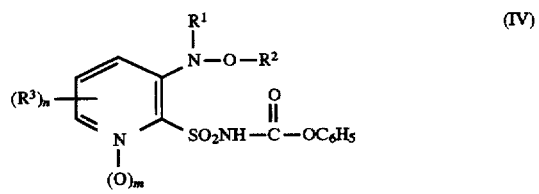

with an amino heterocycle of the formula (V)

$$H-NR^4-A, \qquad (V)$$

or c) reacting a sulfonyl isocyanate of the formula (VI)

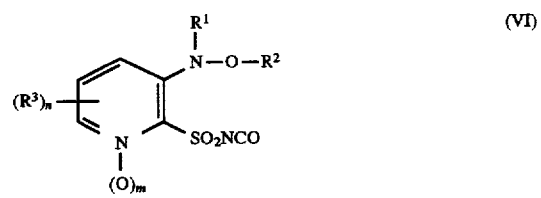

with an amino heterocycle of the formula (V)

$$H-NR^4-A, \qquad (V)$$

or d) first reacting an amino heterocycle of the formula $H-NR^4-A$ (V) with phosgene in a one-pot reaction in the presence of a base, such as, for example, triethylamine, and reacting the intermediate formed with a pyridinesulfonamide of the formula (II), or e) reacting a sulfonamide of the abovementioned formula (II) with a (thio)isocyanate of the formula (VII)

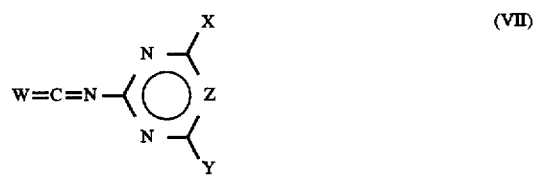

in the presence of a base, for example potassium carbonate or triethylamine, the radicals $R^1$, $R^2$, $R^3$, $R^4$, A, W, X, Y and Z as well as m and n in the formulae (II)–(VII) being as defined in formula (I).

The compounds of the formula (II) and (III) are preferably reacted with base catalysis in an inert organic solvent, such as, for example, dichloromethane, acetonitrile, dioxane or THF, at temperatures between 0° C. and the boiling point of the solvent. The base used is, for example, 1,8-diazabicyclo[5.4.0]undec-7-ene (DBU), triethylamine, trimethylaluminum or triethylaluminum.

The sulfonamides (II) can be prepared from N-protected 3-(N-hydroxylamino)-pyrid-2-ylsulfonamides (VIII)

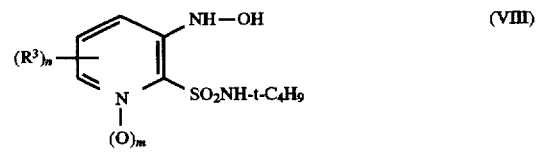

The sulfonamides (II) and the protected sulfonamides (VIII) are novel compounds. These compounds and their preparation are also a subject of the invention.

The compounds of the formula (II) are obtained, for example, starting from compounds of the formula (VIII) by reacting them with carbonyl halides of the formula Hal—CO—R* (Hal=halogen, preferably chlorine) or symmetric or mixed carboxylic anhydrides of the formula R*—CO—O—COR* or of the formula R**—CO—O—COR*, in which R* is defined analogously to R* or R** or is a different aliphatic or aromatic radical, the O-acyl compounds being formed in a first step and the N,O-diacyl compounds being formed when more acylating reagent is added ($R^1$=COR*, and $R^2$=COR**). The diacylated t-butyl-protected sulfonamides which are first obtained are converted into the free sulfonamides (II) ($R^1$=COR*, $R^2$=COR**) using acids, for example trifluoroacetic acid (see below).

Structures of the formula (II) in which $R^1$=COR* and $R^2$=H are obtained by hydrolyzing the above-described N,O-diacyl compounds, for example using dilute sodium hydroxide solution (for example 2N NaOH). Structures of the formula (II) in which $R^1$=H and $R^2$=alkyl are obtained by reacting the compounds of the formula (VIII) with alkylating reagents, such as, for example, methyl iodide or dimethyl sulfate, with an addition of suitable bases, such as, for example, potassium hydroxide, DBU, pyridine, triethylamine or sodium ethanolate. It would then be possible to react these compounds in a further step with acylating reagents, as described above, to give compounds in which $R^1$=COR* and $R^2$=alkyl or substituted alkyl.

Further derivatization can be carried out in analogy to methods known from the literature (see Houben-Weyl, Methoden der organischen Chemie [Methods in Organic Chemistry], Volume E 16a/Part I, pp. 1–419, Dieter Klamann, Georg Thieme Verlag Stuttgart, New York 1990).

The resulting N-tert-butylpyridylsulfonamides can be converted into the compounds of the formula (II) by reaction with a strong acid (for example trifluoroacetic acid).

The individual reaction steps can be carried out analogously to customary processes. The sulfonamides of the formula (VIII) can be prepared from optionally substituted 2-chloro-3-nitropyridines by processes known from the literature. These are first reacted with sulfur-containing nucleophiles, such as, for example, benzylmercaptan, followed by oxidative chlorination of the sulfur atom with sodium hypochlorite or chlorine (formation of the sulfonyl chlorides analogously to EP-A-272 855) and reaction of the sulfonyl chlorides obtained with tert-butylamine to give 3-nitro-2-N-tert-butylsulfonylamidopyridines. The nitro group can subsequently be reduced to the hydroxylamine (II) $R^1=R^2=H$) and then derivatized in a suitable manner, for example by N- or O-acylation, to give different compounds of the formula (II).

Alternatively, compounds of the formula (II) can be prepared from 2-chloro-3-nitropyridines by reducing them to the hydroxylamine, followed by derivatization, the derivatization including, for example, an N- or O-acylation or N- or O-alkylation step, then formation of the sulfonyl chlorides as described above, followed by reaction of the sulfonyl chlorides directly with ammonia by or in analogy to customary methods.

The carbamates of the formula (III) can be prepared by methods described in South African Patent Applications 82/5671 and 82/5045 and EP-A 70804 (U.S. Pat. No. 4,480,101) or Research Disclosure RD 275056.

The compounds (IV) are preferably reacted with the amino heterocycles (V) in inert, aprotic solvents, such as, for example, dioxane, acetonitrile or tetrahydrofuran, at temperatures between 0° C. and the boiling point of the solvent. The pyridylsulfonylcarbamates of the formula (IV) are obtained analogously to EP-A-44 808 or EP-A-237 292.

The pyridylsulfonyl isocyanates of the formula (VI) can be prepared analogously to EP-A-184 385 and reacted with the amino heterocycles of the formula (V).

The (thio)isocyanates of the formula (VII) can be obtained by processes known from the literature (EP-A-232067, EP-A-166516). The (thio)isocyanates (VII) are reacted with compounds (II) at −10° C. and 100° C., preferably 20° to 100° C., in an inert aprotic solvent, such as, for example, acetone or acetonitrile, in the presence of a suitable base, for example $N(C_2H_5)_3$ or $K_2CO_3$.

The salts of the compounds of the formula (I) are preferably prepared in inert solvents, such as, for example, water, methanol or acetone, at temperatures from 0° to 100° C. Bases which are suitable for the preparation of the salts according to the invention are, for example, alkali metal carbonates, such as potassium carbonate, alkali metal hydroxides, alkaline earth metal hydroxides, ammonia or ethanolamine. Acids which are particularly suitable for the salt formation are HCl, HBr, $H_2SO_4$ or $NHO_3$.

The term "inert solvents" in the above process variants is to be understood as meaning in each case solvents which are inert under the specific reaction conditions, but which do not have to be inert under all reaction conditions.

The compounds of the formula (I) according to the invention or salts thereof have an outstanding herbicidal activity against a broad range of economically important monocotyledon and dicotyledon harmful plants. The active substances also act effectively on perennial weeds which are difficult to control and which form shoots from rhizomes, rootstocks or other perennial organs. In this context, it does not matter whether the substances are applied by pre-plant incorporation or pre- or post-emergence. Examples may be mentioned specifically of some representatives of the monocotyledon and dicotyledon weed flora which can be controlled by the compounds according to the invention, without the enumeration being a restriction to certain species.

Examples of weed species on which the active substances act efficiently are, from amongst the monocotyledons, Avena, Lolium, Alopercurus, Phalaris, Echinochloa, Digitaria, Setaria and Cyperus species from the annual sector and, from amongst the perennial species, Agropyron, Cynodon, Imperata and Sorghum, and also perennial Cyperus species.

In the case of the dicotyledon weed species, the spectrum of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention also effect outstanding control on weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage, but then their growth stops, and, eventually, after three to four weeks have elapsed, they die completely.

If the active substances are applied post-emergence to the green parts of the plant, growth equally stops drastically a very short time after the treatment and the weed plants remain at the growth stage at the point in time of application, or they die completely after a certain time, so that, in this manner, competition by the weeds, which is harmful to the crop plants, is eliminated at a very early point in time and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya beans, are not damaged at all, or only to a negligible extent. For these reasons, the present compounds are highly suitable for the selective control of undesired plant growth in plantings for agricultural use.

Moreover, the compounds of the formula (I) according to the invention have outstanding growth-regulating properties in crop plants. They engage in the plant metabolism in a regulating manner and can therefore be employed for the specific control of plant constituents and for facilitating harvesting, for example by triggering desiccation and stunted growth. Moreover, they are also suitable for generally controlling and inhibiting undesired vegetative growth without destroying the plants in the process. Inhibition of the vegetative growth plays an important role in many monocotyledon and dicotyledon crops since it allows lodging to be reduced or prevented completely.

The compounds of the formula (I) according to the invention can be applied in the customary preparations in the form of wettable powders, emulsifiable concentrates, sprayable solutions, dusts or granules. The invention therefore also relates to herbicidal and plant growth-regulating compositions which contain the compounds of the formula (I) or salts thereof.

The compounds of the formula (I) or salts thereof can be formulated in various ways, depending on the prevailing biological and/or chemico-physical parameters. The following examples are suitable possibilities of formulations: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for broadcasting and for soil application, granules (GR) in the form of micro-granules, spray granules, coated granules and adsorption granules, water-dispersible granules (WG), water-soluble granules (SG), ULV formulations, microcapsules and waxes.

These individual types of formulations are known in principle and are described, for example, in: Winnacker-Küchler, "Chemische Technologie" [Chemical Technology], Volume 6, C. Hauser Verlag Munich, 4th Edition 1986, Wade van Valkenburg, "Pesticide Formulations", Marcel Dekker, N.Y., 1973; K. Martens, "Spray Drying" Handbook, 3rd Edition 1979, G. Goodwin Ltd. London.

The formulation auxiliaries required, such as inert materials, surfactants, solvents and further additives are also known and are described, for example, in: Watkins, "Handbook of Insecticide Dust Diluents and Carriers", 2nd Edition, Darland Books, Caldwell, N.J., H. v. Olphen, "Introduction to Clay Colloid Chemistry"; 2nd Edition, J. Wiley & Sons, N.Y.; C. Marsden, "Solvents Guide"; 2nd Edition, Interscience, N.Y. 1963; McCutcheon's "Detergents and Emulsifiers Annual", MC Publ. Corp., Ridgewood, N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag, Munich, 4th Edition, 1986.

Based on these formulations, it is also possible to prepare combinations with other pesticidally active substances, such as, for example, insecticides, acaricides, herbicides, fungicides, safeners, fertilizers and/or growth regulators, for example in the form of a readymix or a tank mix.

Wettable powders are preparations which are uniformly dispersible in water and which, besides the active substance, also contain ionic and/or non-ionic surfactants (wetting agents, dispersants), for example polyoxyethylated alkylphenols, polyoxethylated fatty alcohols, polyoxethylated fatty amines, fatty alcohol polyglycol ether sulfates, alkanesulfonates, alkylbenzenesulfonates, sodium ligninsulfonates, sodium 2,2'-dinaphthylmethane-6,6'-disulfonate, sodium dibutylnaphthalenesulfonates or else sodium oleylmethyltaurinates, in addition to a diluent or inert substance. To prepare the wettable powders, the herbicidal active substances are ground finely, for example in customary apparatuses, such as hammer mills, blower mills and air-jet mills, and the product is mixed with the formulation auxiliaries, either simultaneously or in a subsequent step.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with an addition of one or more ionic and/or non-ionic surfactants (emulsifiers). Examples of emulsifiers which can be used are the following: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan esters, such as, for example sorbitan fatty acid esters, or polyoxyethylene sorbitan esters, such as, for example, polyoxyethylene sorbitan fatty acid esters.

Dusts are obtained by grinding the active substance with finely divided solid substances, for example talc, natural clays, such as kaolin, bentonite and pyrophyllite, or diatomaceous earth.

Suspension concentrates can be water- or oil-based. They can be prepared, for example by wet grinding by means of commercially available bead mills, if appropriate with an addition of surfactants, for example those which have already been mentioned above in the case of the other types of formulations.

Emulsions, for example oil-in-water emulsions (EW) can be prepared, for example, by means of stirrers, colloid mills and/or static mixers using aqueous organic solvents and, if appropriate, surfactants, for example those which have already been mentioned above in the case of the other types of formulations.

Granules can be prepared either by spraying the active substance onto adsorptive, granulated inert material or by applying active substance concentrates to the surface of carriers, such as sand, kaolinites or granulated inert material, with the aid of adhesives, for example polyvinyl alcohol, sodium polyacrylate or else mineral oils. Suitable active substances can also be granulated in the manner which is customary for the preparation of fertilizer granules, if desired in the form of a mixture with fertilizers.

Water-dispersible granules are prepared, as a rule, by customary processes such as spray-drying, fluidized bed granulation, disc granulation, mixing with high-speed mixers and extrusion without solid inert material.

As a rule, the agrochemical preparations contain 0.1 to 99% by weight, in particular 0.1 to 95% by weight, of active substance of the formula (I) or salts thereof.

The active substance concentration in wettable powders is, for example, approximately 10 to 90% by weight, the remainder to 100% by weight is composed of customary formulation components. In the case of emulsifiable concentrates, the active substance concentration can be approximately 1 to 90, preferably 5 to 80, % by weight. Formulations in the form of dusts contain 1 to 30, usually preferably 5 to 20, % by weight of active substance, sprayable solutions approximately 0.05 to 80, preferably 2 to 50, % by weight of active substance. In the case of water-dispersible granules, the active substance content partly depends on whether the active compound is in liquid or solid form and on which granulation auxiliaries, fillers and the like are being used. In the case of the water-dispersible granules, the active substance content is, for example, between 1 and 95% by weight, preferably between 10 and 80% by weight.

Besides, the active substance formulations mentioned optionally contain the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active substances according to the invention in mixed formulations or in tank mixes are, for example, known active substances, as they are described, for example, in Weed Research 26, 441–445 (1986) or "The Pesticide Manual", 9th Edition, The British Crop Protection Council, 1990/91, Bracknell, England, and the literature cited therein. Examples of active substances which may be mentioned as herbicides which are known from the literature and which can be combined with the compounds of the formula (I) are the following (note: either the common names in accordance with the International Organization for Standardization (ISO) or the chemical names, if appropriate together with the customary code number, of the compounds are given): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; bensofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenylacetamide; CDEC, i.e. 2-chloroallyl diethyldithiocarbamate; CGA 184927, i.e. 2-[4-[(5-chloro-3-fluoro-2-pyridinyl)oxy]phenoxy]propanoic acid and its 2-propynyl ester; chlomethoxyfen; chloramben; chlorazifop-butyl, pirifenop-butyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmediphan; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone; clomazon; dimethipin; dimetrasulfuron, cinosulfuron; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; F6285, i.e. 1-[5-(N-methylsulfonyl)amino-2,4-dichlorophenyl]-3-methyl-4-difluoromethyl- 1,2,4-triazol-5-one; fenoprop; fenoxan, s. clomazon; fenoxaprop-ethyl; fenuron; flamprop-methyl; flazasulfuron; fluazifop and its ester derivatives; fluchloralin; flumetsulam; N-[2,6-difluorophenyl]-5-methyl-(1,2,4)-triazolo[1,5a]pyrimidin-2-sulfonamide; flumeturon; flumipropyn; fluorodifen; fluoroglycofen-ethyl; fluridone; flurochloridone; fluroxypyr; flurtamone; fomesafen; fosamine; furyloxyfen; glufosinate; glyphosate; halosaten; haloxyfop and its ester derivatives; hexazinone; Hw 52, i.e. N-(2,3-dichlorophenyl)-4-(ethoxymethoxy)benzamide; imazamethabenz-methyl; imazapyr; imazaquin; imazethamethapyr; imazethapyr; imazosulfuron; ioxynil; isocarbamide; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldaimuron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazineamine; MT 5950, i.e. N-[3-chloro-4-(1-methylethyl)phenyl]-2-methylpentaneamide; naproanilide; naproamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzaline; oxadiazon; oxyfluorfen; paraquat; pebulate; pendimethalin; perfluidone; phenmedipham; phenisopham; phenmedipham; picloram; piperophos; piributicarb; pirifenop-butyl, pretilachlor; primisulfuron-methyl; procyazine; prodiamine; profluralin; proglinazine-ethyl; prometon; prometryn; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives; quizalofop and its ester derivatives; quizalofop-ethyl; quizalofop-p-tefuryl; renriduron; daimuron; S 275, i.e. 2-[4-chloro-2-fluoro-5-(2-propynyloxy)phenyl]-4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfometuron-methyl; sulfazuron; flazasulfuron; TCA; tebutam; tebuthiuron; terbacil; terbucarb; terbuchlor; terbumeton; terbuthylazine; terbutryn; TFH 450, i.e. N,N-diethyl-3-[(2-ethyl-6methylphenyl)sulfonyl]-1H-1,2,4-triazole-1-carboxamide; thiazafluoron; thifensulfuron-methyl; thiobencarb; tiocarbazil; tralkoxydim; tri-allate; triasulfuron; triazofenamide; tribenuronmethyl; triclopyr; tridiphane; trietazine; trifluralin; trimeturon; vernolate; WL 110547; i.e. 5-phenoxy-1-[3-(trifluoromethyl)phenyl]-1H-tetrazole.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application and for broadcasting and sprayable solutions are conventionally not diluted any further with inert substances prior to use.

The compounds according to the invention can be applied, for example, directly to the harmful plants or to the harmful plants and crop plants simultaneously by the post-emergence method, or to the area on which the plants grow, for example, to field soil containing seeds of plants or emerged plants, or to areas under cultivation, such as, for example, a rice-growing area, either pre- or post-emergence.

The application rate required, of the compounds of the formula (I), varies with the external conditions such as, inter alia, temperature, humidity and the type of herbicide used. It can vary within wide limits, for example between 0.001 and 10.0 kg/ha or more of active ingredient, but it is preferably between 0.005 and 5 kg/ha.

A. CHEMICAL EXAMPLES

Examples a) 2-Benzylthio-3-nitropyridine 39.1 g (0.315 mol) of benzylmercaptan are introduced into 200 ml of acetonitrile, 47.8 g (0.346 mol) of $K_2CO_3$ are added, and the mixture is stirred for 40 minutes at 60° C. 50.0 g (0.315 mol) of 2-chloro-3-nitropyridine dissolved in 150 ml of acetonitrile are subsequently added dropwise, and the mixture is refluxed for 4 hours. The acetonitrile is distilled off under reduced pressure, the residue is taken up in dichloromethane, the organic phase is washed once using saturated sodium hydrogen carbonate solution and once using 1N hydrochloric acid and dried over magnesium sulfate, the desiccant is filtered off, and the dichloromethane is removed under reduced pressure. Recrystallization from methanol gives 60.9 g (79% of theory) of 2-benzyl-3-nitropyridine of melting point 72° C.

b) 3-Nitro-3-pyridine-tert-butylsulfonamide 24.6 g (0.1 mol) of 2-benzylthio-3-nitropyridine are dissolved in 360 ml of CH$_2$Cl$_2$. 280 ml of water are added, and 44.9 ml of concentrated HCl are added dropwise at 0° C. 550 ml of 5% sodium hypochlorite solution are subsequently run in at such a rate that the internal temperature does not exceed 5° C. After stirring has been continued for 30 minutes at 0° C., the batch is poured into 500 ml of water, the organic phase is separated off, and the aqueous phase is washed at 0° C. using CH$_2$Cl$_2$. The combined organic phases are subsequently washed using NaCl solution and dried over MgSO$_4$. At −70° C., 32.1 g (0.44 mol) of t-butylamine are then added dropwise. The batch is allowed to come to room temperature, poured into water and brought to a pH of 2–3 using 1N HCl. After the organic phase has been separated off, the aqueous phase is subsequently washed with CH$_2$Cl$_2$, the organic phases are combined and dried, and the solvent is stripped off under reduced pressure. After the residue has been extracted by stirring with diethyl ether and filtered, 14.7 g (57% of theory) of 3-nitro-2-pyridine-tert-butylsulfonamide of melting point 134° C. are obtained.

c) 3-N-Hydroxylamino-2-pyridine-tert-butylsulfonamide 45.70 g of zinc dust were added in portions with ice-cooling to a homogeneous solution of 38.40 g (148.3 mmol) of 3-nitro-2-pyridine-tert-butylsulfonamide and 21.89 g (409.2 mmol) of ammonium chloride in 600 ml of ethanol and 150 ml of water. After the addition had ended, stirring was continued for 30 minutes, excess zinc was then filtered off, and the filtrate was evaporated to dryness in vacuo. Inorganic constituents of the residues were separated off by suspending the residue in a little ethyl acetate and filtering through a silica gel column (height 5 cm, Ø 5 cm) in ethyl acetate. The filtrate was concentrated and crystallized from ethyl acetate, petroleum ether (1:3). 32.9 g of 3-N-hydroxylamino-2-pyridine-tert-butylsulfonamide (yield 90%) of a melting point of 129° C. were obtained.

d) 3-N-(O-Acetyl)hydroxylamino-2-pyridine-tert-butylsulfonamide 0.88 g (4.10 mmol) of 3-N-hydroxylamino-2-pyridine-tert-butylsulfonamide together with 0.50 [lacuna] (4.9 mmol) of triethylamine were dissolved in 10 ml of anhydrous tetrahydrofuran, and 0.32 g (4.1 mmol) of acetyl chloride was added to this solution. After 30 minutes, 100 ml of ethyl acetate were added, the mixture was extracted twice using 2N HCl, the organic phase was dried using Na$_2$SO$_4$, the solvent was filtered off, and the filtrate was concentrated on a rotary evaporator. The crude product was crystallized from ethyl.acetate/n-heptane. 1.10 g of 3-N-(O-acetyl)hydroxylamino-2-pyridine-tert-butylsulfonamide was obtained as a crystalline solid (m.p. 147° C., yield 93%).

e) 3-N-(O-Acetyl)hydroxylamino-2-pyridinesulfonamide 2.00 [lacuna] (6.97 mmol) of 3-N-(O-acetyl)hydroxylamino-2-pyridine-tert-butylsulfonamide were heated for 3 hours at 60° C. in 3.0 ml of trifluoroacetic acid. After the solvent had been removed in vacuo, the residue was crystallized from ethyl acetate/ether. 1.21 g (yield 75%) of 3-N-(O-acetyl)hydroxylamino-2-pyridinesulfonamide of melting point 121° C. were obtained.

f) 3-(4,6-Dimethoxypyrimidin-2-yl)-1-[(3-N-(O-acetyl)hydroxylamino)-2-pyridylsulfonylurea 844 mg (6.12 mmol) of 1,5-diazabicyclo[5.4.0]undec-7-ene (DBU) were added to a solution of 1.20 g (5.10 mmol) of 3-N-(O-acetyl)hydroxylamino-2-pyridylsulfonamide and 2.00 g (7.3 mmol) of 1-phenyl-3-(4,6-dimethoxypyrimidin-2-yl)carbamate in 20 ml of acetonitrile. After the mixture had been stirred for 30 minutes at room temperature, it was acidified using 2N hydrochloric acid and extracted repeatedly using ethyl acetate, and the extract was dried over Na$_2$SO$_4$, filtered and evaporated on a rotary evaporator. The product crystallized from ethyl acetate/ethanol 1:10. 0.93 g (44% yield) of melting point 122° C. was obtained.

g) 3-N-(O-Methyl)hydroxylamino-2-pyridine-tert-butylsulfonamide 6.00 g (24.5 mmol) of 3-N-hydroxylamino-2-pyridine-tert-butylsulfonamide together with 3.39 g (26.9 mmol) of dimethyl sulfate were dissolved in 200 ml of anhydrous THF, the solution was cooled to −20° C., and 5.54 g (49.0 mmol) of potassium tert-butylate were subsequently added in portions. Within 2 hours, the reaction solution came to room temperature. 100 ml of water were then added and the mixture was extracted repeatedly using ether. After the ether phases had been dried over sodium sulfate, a crude product was obtained which was chromatographed over silica gel using ethyl acetate/n-heptane 1:2 as the eluent. 2.56 g (40%) of 3-N-(O-methyl)hydroxylamino-2-pyridine-tert-butylsulfonamide were obtained in the form of colorless crystals of melting point 128° C.

h) 3-N-(O-methyl)hydroxylamino-2-pyridinesulfonamide 1.00 g (3.86 mmol) of 3-N-(Omethyl)hydroxylamino-2-pyridine-tert-butylsulfonamide were dissolved in 15 ml of trifluoroacetic acid and the mixture was heated for 8 hours at 50° C. The solvent was then removed in vacuo and the residue was crystallized from ethyl acetate/cyclohexane. 470 mg (61%) of 3-N-(O-methyl)hydroxylamino-2-pyridinesulfonamide of melting point 149° C. were obtained.

i) 3-(4,6-Dimethoxypyrimidin-2-yl)-1-[3-N-[O-methyl]hydroxylamino)-2-pyridylsulfonyl]urea 430 mg (2.11 mmol) of 3-N-(O-methyl)hydroxylamino-2-pyridinesulfonamide together with 7.57 mg (2.75 mmol) of 1-phenyl-3(4,6-dimethoxypyrimidin-2-yl)carbamate were dissolved in 20 ml of acetonitrile, and 0.350 g (2.53 mmol) of 1,8-diazabicyclo[5.4.0]undec-7-ene was added at room temperature. After 30 minutes, the mixture acidified using 2N hydrochloric acid, extracted using ethyl acetate, dried over Na$_2$SO$_4$ and filtered, and the filtrate concentrated on a rotary evaporator. The product crystallized from methylene chloride/ether. 450 mg (55% of theory) of 3-(4,6-dimethoxypyrimidin-2-yl)-1-[3-N[O-methyl]hydroxylamino)-2-pyridylsulfonyl]urea of melting point 138° C. were obtained.

The other compounds of Tables 1–5 which follow were obtained analogously to the processes of Examples a to i.

Abbreviations in Tables 1–5:

M.p.=melting point in °C.

Ph=phenyl

Bzl=benzyl

Me=methyl

Et=ethyl

Pr=propyl

Bu=butyl n-Alkyl=straight-chain alkyl=alkyl i-Alkyl=iso-alkyl (for example i-Bu=isobutyl)

s-Alkyl=secondary alkyl t-Alkyl=tertiary alkyl c-Alkyl=cycloalkyl (for example c-Pr=cyclopropyl)

TABLE 1

Compounds of the formula (Ia)

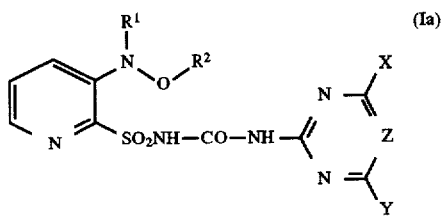

| Ex | R¹ | R² | X | Y | Z | M.p. |
|---|---|---|---|---|---|---|
| 1 | H | COCH₃ | OCH₃ | OCH₃ | CH | 121–122 |
| 2 | H | " | OCH₃ | CH₃ | CH | |
| 3 | H | " | OCH₃ | Cl | CH | |
| 4 | H | " | CH₃ | CH₃ | CH | |
| 5 | H | " | OCH₃ | OCH₃ | N | |
| 6 | H | " | OCH₃ | CH₃ | N | |
| 7 | H | " | OC₂H₅ | NHCH₃ | N | |
| 8 | H | COC₂H₅ | OCH₃ | OCH₃ | CH | 108–109 |
| 9 | H | " | OCH₃ | CH₃ | CH | |
| 10 | H | " | OCH₃ | Cl | CH | |
| 11 | H | " | CH₃ | CH₃ | CH | |
| 12 | H | " | OCH₃ | OCH₃ | N | |
| 13 | H | " | OCH₃ | CH₃ | N | |
| 14 | H | " | OC₂H₅ | NHCH₃ | N | |
| 15 | H | CO-i-Pr | OCH₃ | OCH₃ | CH | 102 |
| 16 | H | CO-i-Pr | OCH₃ | CH₃ | CH | |
| 17 | H | CO-i-Pr | OCH₃ | Cl | CH | |
| 18 | H | " | CH₃ | CH₃ | CH | |
| 19 | H | " | OCH₃ | OCH₃ | N | |
| 20 | H | " | OCH₃ | CH₃ | N | |
| 21 | H | " | OC₂H₅ | NHCH₃ | N | |
| 22 | H | " | OCH₃ | OCH₃ | CH | |
| 23 | H | CO-t-Bu | OCH₃ | CH₃ | CH | 121–122 |
| 24 | H | " | OCH₃ | Cl | CH | |
| 25 | H | " | CH₃ | CH₃ | CH | |
| 26 | H | " | OCH₃ | OCH₃ | N | |
| 27 | H | " | OCH₃ | CH₃ | N | |
| 28 | H | " | OC₂H₅ | NHCH₃ | N | |
| 29 | H | CO-benzyl | OCH₃ | OCH₃ | CH | 112–115 |
| 30 | H | " | OCH₃ | CH₃ | CH | |
| 31 | H | " | OCH₃ | Cl | CH | |
| 32 | H | " | CH₃ | CH₃ | CH | |
| 33 | H | " | OCH₃ | OCH₃ | N | |
| 34 | H | " | OCH₃ | CH₃ | N | |
| 35 | H | " | OC₂H₅ | NHCH₃ | N | |
| 36 | H | CO—CH₂—O—CH₃ | OCH₃ | OCH₃ | CH | 108–109 |
| 37 | H | " | OCH₃ | CH₃ | CH | |
| 38 | H | " | OCH₃ | Cl | CH | |
| 39 | H | " | CH₃ | CH₃ | CH | |
| 40 | H | " | OCH₃ | OCH₃ | N | |
| 41 | H | CO—CH₂—O—CH₃ | OCH₃ | CH₃ | N | |
| 42 | H | " | OC₂H₅ | NHCH₃ | N | |
| 43 | H | CO-n-pentyl | OCH₃ | OCH₃ | CH | 124 |
| 44 | H | " | OCH₃ | CH₃ | CH | |
| 45 | H | " | OCH₃ | Cl | CH | |
| 46 | H | " | CH₃ | CH₃ | CH | |
| 47 | H | " | OCH₃ | OCH₃ | N | |
| 48 | H | " | OCH₃ | CH | N | |
| 49 | H | " | OC₂H₅ | NHCH₃ | N | |
| 50 | H | CO—CH₂Cl | OCH₃ | OCH₃ | CH | |
| 51 | H | CO—CHCl₂ | OCH₃ | OCH₃ | CH | |
| 52 | H | CO—CCl₃ | OCH₃ | OCH₃ | CH | |
| 53 | H | CO—CF₃ | OCH₃ | OCH₃ | CH | |
| 54 | H | CO—CH₂F | O—CH₃ | OCH₃ | | |
| 55 | H | CO-cyclobutyl | OCH₃ | OCH₃ | CH | |
| 56 | H | CO-cyclopropyl | OCH₃ | OCH₃ | CH | 118–120 |
| 57 | H | " | OCH₃ | OCH₃ | CH | |
| 58 | H | " | OCH₃ | Cl | CH | |
| 59 | H | " | CH₃ | CH₃ | CH | |
| 60 | H | " | OCH₃ | OCH₃ | N | |
| 61 | H | " | OCH₃ | CH₃ | N | |
| 62 | H | " | OC₂H₅ | NHCH₃ | N | |
| 63 | H | CO—CH=CH₂ | OCH₃ | OCH₃ | CH | |
| 64 | H | CO—CH₂—CH=CH₂ | OCH₃ | OCH₃ | CH | |

TABLE 1-continued

Compounds of the formula (Ia)

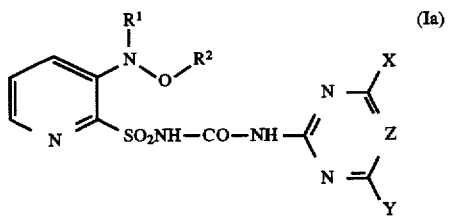

| Ex | R¹ | R² | X | Y | Z | M.p. |
|---|---|---|---|---|---|---|
| 65 | H | CO-phenyl | OCH₃ | OCH₃ | CH | |
| 66 | H | CO—S—Bu | OCH₃ | OCH₃ | CH | |
| 67 | H | COCH₂Br | OCH₃ | OCH₃ | CH | |
| 68 | H | COCH₂CN | OCH₃ | OCH₃ | CH | |
| 69 | H | CO₂CH₃ | OCH₃ | OCH₃ | CH | 152 |
| 70 | H | " | OCH₃ | CH₃ | CH | |
| 71 | H | " | OCH₂ | Cl | CH | |
| 72 | H | " | CH₃ | CH₃ | CH | |
| 73 | H | " | OCH₃ | OCH₃ | N | |
| 74 | H | " | OCH₃ | CH₃ | N | |
| 75 | H | " | OC₂H₅ | NHCH₃ | N | |
| 76 | H | CO₂C₂H₅ | OCH₃ | OCH₃ | CH | 116–117 |
| 77 | H | " | OCH₃ | OCH₃ | CH | |
| 78 | H | " | OCH₃ | CH₃ | CH | |
| 79 | H | " | OCH₃ | Cl | CH | |
| 80 | H | " | CH₃ | CH₃ | CH | |
| 81 | H | " | OCH₃ | OCH₃ | N | |
| 82 | H | " | OCH₃ | CH₃ | N | |
| 83 | H | " | OC₂H₅ | NHCH₃ | N | |
| 84 | H | CONHCH₃ | OCH₃ | OCH₃ | CH | |
| 85 | H | CON(CH₃)₂ | OCH₃ | OCH₃ | CH | |
| 86 | H | CON(pyrrolidinyl) | OCH₃ | OCH₃ | CH | |
| 87 | H | CON(piperidinyl) | OCH₃ | OCH₃ | CH | |
| 88 | H | CON(morpholinyl) | OCH₃ | OCH₃ | CH | |
| 89 | H | CONHC₂H₅ | OCH₃ | OCH₃ | CH | |
| 90 | H | H | OCH₃ | OCH₃ | CH | 121–124 |
| 91 | H | " | OCH₃ | CH₃ | CH | |
| 92 | H | " | OCH₃ | Cl | CH | |
| 93 | H | " | CH₃ | CH₃ | CH | |
| 94 | H | " | OCH₃ | OCH₃ | N | |
| 95 | H | " | OCH₃ | CH₃ | N | |
| 96 | H | " | OCH₃ | NHCH₃ | N | |
| 97 | H | CH₃ | OCH₃ | OCH₃ | CH | 138° C. |
| 98 | H | " | OCH₃ | CH₃ | CH | |
| 99 | H | " | OCH₃ | Cl | CH | |
| 100 | H | " | CH₃ | CH₃ | CH | |
| 101 | H | " | OCH₃ | OCH₃ | N | |
| 102 | H | " | OCH₃ | CH₃ | N | |
| 103 | H | " | OC₂H₅ | NHCH₃ | N | |
| 104 | H | C₂H₅ | OCH₃ | OCH₃ | CH | 138° C. |
| 105 | H | " | OCH₃ | CH₃ | CH | |
| 106 | H | " | OCH₃ | Cl | CH | |
| 107 | H | " | CH₃ | CH₃ | CH | |
| 108 | H | " | OCH₃ | OCH₃ | N | |
| 109 | H | " | OCH₃ | CH₃ | N | |
| 110 | H | " | OC₂H₅ | NHCH₃ | N | |
| 111 | H | n-C₃H₇ | OCH₃ | OCH₃ | CH | 124–126 |
| 112 | H | " | OCH₃ | CH₃ | CH | |
| 113 | H | " | OCH₃ | Cl | CH | |
| 114 | H | " | CH₃ | CH₃ | CH | |

TABLE 1-continued

Compounds of the formula (Ia)

$$\text{(Ia)}$$

| Ex | R¹ | R² | X | Y | Z | M.p. |
|---|---|---|---|---|---|---|
| 115 | H | " | OCH₃ | OCH₃ | N | |
| 116 | H | " | OCH₃ | CH₃ | N | |
| 117 | H | " | OC₂H₅ | NHCH₃ | N | |
| 118 | H | iso-C₃H₇ | OCH₃ | OCH₃ | CH | 140 |
| 119 | H | " | OCH₃ | CH₃ | CH | |
| 120 | H | " | OCH₃ | Cl | CH | |
| 121 | H | " | CH₃ | CH₃ | CH | |
| 122 | H | " | OCH₃ | OCH₃ | N | |
| 123 | H | " | OCH₃ | CH₃ | N | |
| 124 | H | " | OC₂H₅ | NHCH₃ | N | |
| 125 | H | iBu | OCH₃ | OCH₃ | CH | 130–132 |
| 126 | H | " | CH₃ | OCH₃ | CH | |
| 127 | H | " | OCH₃ | OCH₃ | N | |
| 128 | H | " | OCH₃ | CH₃ | N | |
| 129 | H | " | OC₂H₅ | NHCH₃ | N | |
| 130 | N | CH₂CF₃ | OCH₃ | OCH₃ | CH | |
| 131 | H | " | OCH₃ | CH₃ | CH | |
| 132 | H | " | OCH₃ | Cl | CH | |
| 133 | H | " | CH₃ | CH₃ | CH | |
| 134 | H | " | OCH₃ | OCH₃ | N | |
| 135 | H | CH₂CF₃ | OCH₃ | CH₃ | N | |
| 136 | H | " | OC₂H₅ | NHCH₃ | N | |
| 137 | H | CH₂—CH₂Br | OCH₃ | OCH₃ | CH | |
| 138 | H | " | OCH₃ | CH₃ | CH | |
| 139 | H | " | OCH₃ | Cl | CH | |
| 140 | H | " | CH₃ | CH₃ | CH | |
| 141 | H | " | OCH₃ | OCH₃ | N | |
| 142 | H | " | OCH₃ | CH₃ | N | |
| 143 | H | " | OC₂H₅ | NHCH₃ | N | |
| 144 | H | CH₂CH₂OCH₃ | OCH₃ | OCH₃ | CH | |
| 145 | H | " | OCH₃ | CH₃ | CH | |
| 146 | H | " | OCH₃ | Cl | CH | |
| 147 | H | " | CH₃ | CH₃ | CH | |
| 148 | H | " | OCH₃ | OCH₃ | N | |
| 149 | H | " | OCH₃ | CH₃ | N | |
| 150 | H | " | OC₂H₅ | NHCH₃ | N | |
| 151 | H | CH₂F | OCH₃ | OCH₃ | CH | |
| 152 | | " | OCH₃ | CH₃ | CH | |
| 153 | | " | OCH₃ | Cl | CH | |
| 154 | | " | CH₃ | CH₃ | CH | |
| 155 | | " | OCH₃ | OCH₃ | N | |
| 156 | | " | OCH₃ | CH₃ | N | |
| 157 | | " | OC₂H₅ | NHCH₃ | N | |
| 158 | H | CH₂CN | OCH₃ | OCH₃ | CH | |
| 159 | H | cyclopropylmethyl | OCH₃ | OCH₃ | CH | |
| 160 | H | CH₂—Ph | OCH₃ | OCH₃ | CH | |
| 161 | H | CH₂—Br | OCH₃ | OCH₃ | CH | |
| 162 | H | CH₂CH₂—S—CH₃ | OCH₃ | OCH₃ | CH | |
| 163 | H | CH₂—CH=CH₂ | OCH₃ | OCH₃ | CH | |
| 164 | H | CH₂—C≡CH | OCH₃ | OCH₃ | CH | |
| 165 | H | Si(CH₃)₃ | OCH₃ | OCH₃ | CH | |
| 166 | H | " | OCH₃ | CH₃ | CH | |
| 167 | H | " | OCH₃ | Cl | CH | |
| 168 | H | " | CH₃ | CH₃ | CH | |
| 169 | H | " | OCH₃ | OCH₃ | N | |
| 170 | H | " | OCH₃ | CH₃ | N | |
| 171 | H | Si(CH₃)₃ | OC₂H₅ | NHCH₃ | N | |
| 172 | H | Si(CH₃)₂-tert-butyl | OCH₃ | OCH₃ | CH | |
| 173 | H | " | OCH₃ | CH₃ | CH | |
| 174 | H | " | OCH₃ | Cl | CH | |
| 175 | H | " | CH₃ | CH₃ | CH | |
| 176 | H | " | OCH₃ | OCH₃ | N | |
| 177 | H | " | OCH₃ | CH₃ | N | |

TABLE 1-continued

Compounds of the formula (Ia)

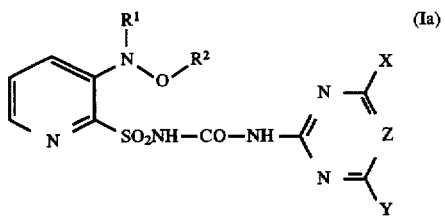

| Ex | $R^1$ | $R^2$ | X | Y | Z | M.p. |
|---|---|---|---|---|---|---|
| 178 | H | " | $OC_2H_5$ | $NHCH_3$ | N | |
| 179 | H | $Si(C_2H_5)_3$ | $OCH_3$ | $OCH_3$ | CH | |
| 180 | H | " | $OCH_3$ | $CH_3$ | CH | |
| 181 | H | " | $OCH_3$ | Cl | CH | |
| 182 | H | " | $CH_3$ | $CH_3$ | CH | |
| 183 | H | " | $OCH_3$ | $OCH_3$ | N | |
| 184 | | | $OCH_3$ | $CH_3$ | N | |
| 185 | | | $OC_2H_5$ | $NHCH_3$ | N | |
| 186 | $CH_3$ | $CH_3$ | $OCH_3$ | $OCH_3$ | CH | 198 |
| 187 | $CH_3$ | " | $OCH_3$ | $CH_3$ | CH | |
| 188 | $CH_3$ | " | $OCH_3$ | Cl | CH | |
| 189 | $CH_3$ | " | $OCH_3$ | $OCH_3$ | N | |
| 190 | $CH_3$ | " | $OCH_3$ | $CH_3$ | N | |
| 191 | $CH_3$ | " | $OC_2H_5$ | $NHCH_3$ | N | |
| 192 | $C_2H_5$ | $CH_3$ | $OCH_3$ | $OCH_3$ | CH | |
| 193 | " | " | $OCH_3$ | $CH_3$ | CH | |
| 194 | $C_2H_5$ | $CH_3$ | $OCH_3$ | Cl | CH | |
| 195 | " | " | $OCH_3$ | $OCH_3$ | N | |
| 196 | " | " | $OCH_3$ | $CH_3$ | N | |
| 197 | " | " | $OC_2H_5$ | $NHCH_3$ | N | |
| 198 | $CH_2CF_3$ | $CH_3$ | $OCH_3$ | $OCH_3$ | CH | |
| 199 | " | " | $OCH_3$ | $CH_3$ | CH | |
| 200 | " | " | $OCH_3$ | Cl | CH | |
| 201 | " | " | $OCH_3$ | $OCH_3$ | N | |
| 202 | " | " | $OCH_3$ | $CH_3$ | N | |
| 203 | " | " | $OC_2H_5$ | $NHCH_3$ | N | |
| 204 | $n-C_3H_7$ | $CH_3$ | $OCH_3$ | $OCH_3$ | CH | |
| 205 | " | " | $OCH_3$ | $CH_3$ | CH | |
| 206 | " | " | $OCH_3$ | Cl | CH | |
| 207 | " | " | $OCH_3$ | $OCH_3$ | N | |
| 208 | " | " | $OCH_3$ | $CH_3$ | N | |
| 209 | " | " | $OC_2H_5$ | $NHCH_3$ | N | |
| 210 | $iso-C_3H_7$ | $CH_3$ | $OCH_3$ | $OCH_3$ | CH | |
| 211 | " | " | $OCH_3$ | $CH_3$ | CH | |
| 212 | " | " | $OCH_3$ | Cl | CH | |
| 213 | " | " | $OCH_3$ | $OCH_3$ | N | |
| 214 | " | " | $OCH_3$ | $CH_3$ | N | |
| 215 | " | " | $OC_2H_5$ | $NHCH_3$ | N | |
| 216 | $CH_2CH_2Cl$ | $CH_3$ | $OCH_3$ | $OCH_3$ | CH | |
| 217 | $CH_2CH_2Cl$ | $CH_3$ | $OCH_3$ | $CH_3$ | CH | |
| 218 | " | " | $OCH_3$ | Cl | CH | |
| 219 | " | " | $OCH_3$ | $OCH_3$ | N | |
| 220 | " | " | $OCH_3$ | $CH_3$ | N | |
| 221 | " | " | $OC_2H_5$ | $NHCH_3$ | N | |
| 222 | $CH_2CHCl_2$ | $CH_3$ | $OCH_3$ | $OCH_3$ | CH | |
| 223 | $CH_2CCl_3$ | $CH_3$ | $OCH_3$ | $OCH_3$ | CH | |
| 224 | benzyl | $CH_3$ | $OCH_3$ | $OCH_3$ | CH | |
| 225 | $C_2H_5$ | $C_2H_5$ | $OCH_3$ | $OCH_3$ | CH | 163° C. |
| 226 | $CH_2CF_3$ | $C_2H_5$ | $OCH_3$ | $OCH_3$ | CH | |
| 227 | $n-C_3H_7$ | $C_2H_5$ | $OCH_3$ | $OCH_3$ | CH | |
| 228 | $iso-C_3H_7$ | $C_2H_5$ | $OCH_3$ | $OCH_3$ | CH | |
| 229 | $CH_2CH_2Cl$ | $C_2H_5$ | $OCH_3$ | $OCH_3$ | CH | |
| 230 | $CH_2CHCl_2$ | $C_2H_5$ | $OCH_3$ | $OCH_3$ | CH | |
| 231 | $C_2CCl_3$ | $C_2H_5$ | $OCH_3$ | $OCH_3$ | CH | |
| 232 | cyclopropyl-methyl | $CH_3$ | $OCH_3$ | $OCH_3$ | CH | |
| 233 | $CH_3$ | $C_2H_5$ | $OCH_3$ | $OCH_3$ | CH | |
| 234 | " | " | $OCH_3$ | $CH_3$ | CH | |
| 235 | " | " | $OCH_3$ | Cl | CH | |
| 236 | " | " | $OCH_3$ | $OCH_3$ | N | |
| 237 | " | " | $OCH_3$ | CH | N | |
| 238 | " | " | $OC_2H_5$ | $NHCH_3$ | N | |
| 239 | $CH_3$ | $CH_2CF_3$ | $OCH_3$ | $OCH_3$ | CH | |
| 240 | $CH_3$ | $CH_2CF_3$ | $OCH_3$ | $CH_3$ | CH | |

TABLE 1-continued

Compounds of the formula (Ia)

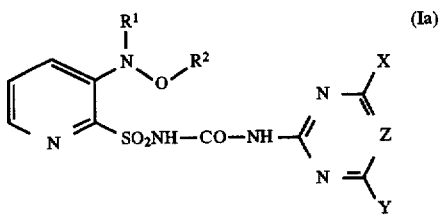

| Ex | $R^1$ | $R^2$ | X | Y | Z | M.p. |
|---|---|---|---|---|---|---|
| 241 | " | " | CCH$_3$ | Cl | CH | |
| 242 | " | " | OCH$_3$ | OCH$_3$ | N | |
| 243 | " | " | OCH$_3$ | CH$_3$ | N | |
| 244 | " | " | OC$_2$H$_5$ | NHCH$_3$ | N | |
| 245 | CH$_3$ | n-Pr | OCH$_3$ | OCH$_3$ | CH | |
| 246 | " | " | OCH$_3$ | CH$_3$ | CH | |
| 247 | " | " | OCH$_3$ | Cl | CH | |
| 248 | " | " | OCH$_3$ | OCH$_3$ | N | |
| 249 | " | " | OCH$_3$ | CH$_3$ | N | |
| 250 | " | " | OC$_2$H$_5$ | NHCH$_3$ | N | |
| 251 | CH$_3$ | iso-C$_3$H$_7$ | OCH$_3$ | OCH$_3$ | CH | |
| 252 | " | " | OCH$_3$ | CH$_3$ | CH | |
| 253 | " | " | OCH$_3$ | Cl | CH | |
| 254 | " | " | OCH$_3$ | OCH$_3$ | N | |
| 255 | " | " | OCH$_3$ | CH$_3$ | N | |
| 256 | " | " | OC$_2$H$_5$ | NHCH$_3$ | N | |
| 257 | CH$_3$ | CH$_2$CH$_2$Cl | OCH$_3$ | OCH$_3$ | CH | |
| 256 | " | " | OCH$_3$ | CH$_3$ | CH | |
| 259 | " | " | OCH$_3$ | Cl | CH | |
| 260 | " | " | OCH$_3$ | OCH$_3$ | N | |
| 261 | " | " | OCH$_3$ | CH$_3$ | N | |
| 262 | " | " | OC$_2$H$_5$ | NHCH$_3$ | N | |
| 253 | CH$_3$ | CH$_2$CHCl$_2$ | OCH$_3$ | OCH$_3$ | CH | |
| 284 | CH$_3$ | CH$_2$CCl$_3$ | OCH$_3$ | OCH$_3$ | CH | |
| 265 | CH$_3$ | benzyl | OCH$_3$ | OCH$_3$ | CH | |
| 266 | CH$_3$ | CH$_2$CH$_2$—OCH$_3$ | OCH$_3$ | OCH$_3$ | CH | |
| 267 | CH$_3$ | CH$_2$CH$_2$—SCH$_3$ | OCH$_3$ | OCH$_3$ | CH | |
| 268 | C$_2$H$_5$ | CH$_2$CF$_3$ | OCH$_3$ | OCH$_3$ | CH | |
| 269 | C$_2$H$_5$ | n-C$_3$H$_7$ | OCH$_3$ | OCH$_3$ | CH | |
| 270 | C$_2$H$_7$ | iso-C$_3$H$_7$ | OCH$_3$ | OCH$_3$ | CH | |
| 271 | C$_2$H$_5$ | CH$_2$CH$_2$Cl | OCH$_3$ | OCH$_3$ | CH | |
| 272 | C$_2$H$_5$ | CH$_2$CHCl$_2$ | OCH$_3$ | OCH$_3$ | CH | |
| 273 | C$_2$H$_5$ | CH$_2$CCl$_3$ | OCH$_3$ | OCH$_3$ | CH | |
| 274 | C$_2$H$_5$ | cyclopropylmethyl | OCH$_3$ | OCH$_3$ | CH | |
| 275 | CH$_3$ | cyclopropylmethyl | OCH$_3$ | OCH$_3$ | CH | |
| 276 | CH$_3$ | CH$_2$F | OCH$_3$ | OCH$_3$ | CH | |
| 277 | CH$_3$ | CHF$_2$ | OCH$_3$ | OCH$_3$ | CH | |
| 278 | CH$_3$ | CF$_3$ | OCH$_3$ | OCH$_3$ | CH | |
| 279 | CH$_3$ | Si(CH$_3$)$_3$ | OCH$_3$ | OCH$_3$ | CH | |
| 280 | " | " | OCH$_3$ | CH$_3$ | CH | |
| 281 | " | " | OCH$_3$ | Cl | CH | |
| 282 | " | " | CH$_3$ | CH$_3$ | CH | |
| 283 | " | " | OCH$_3$ | OCH$_3$ | N | |
| 284 | " | " | OCH$_3$ | CH$_3$ | N | |
| 285 | " | " | OC$_2$H$_5$ | NHCH$_3$ | N | |
| 286 | CH$_3$ | Si(C$_2$H$_5$)$_3$ | OCH$_3$ | OCH$_3$ | CH | |
| 287 | " | " | OCH$_3$ | CH$_3$ | CH | |
| 288 | " | " | OCH$_3$ | Cl | CH | |
| 289 | " | " | CH$_3$ | CH$_3$ | CH | |
| 290 | " | " | OCH$_3$ | OCH$_3$ | N | |
| 291 | " | " | OCH$_3$ | CH$_3$ | N | |
| 292 | " | " | OC$_2$H$_5$ | NHCH$_3$ | N | |
| 293 | CH$_3$ | Si(CH$_3$)$_2$t-Bu | OCH$_3$ | OCH$_3$ | CH | |
| 294 | " | " | OCH$_3$ | CH$_3$ | CH | |
| 295 | " | " | OCH$_3$ | Cl | CH | |
| 296 | " | " | CH$_3$ | CH$_3$ | CH | |
| 297 | " | " | OCH$_3$ | OCH$_3$ | N | |
| 298 | " | " | OCH$_3$ | CH$_3$ | N | |
| 299 | " | " | OC$_2$H$_5$ | NHCH$_3$ | N | |
| 300 | C$_2$H$_5$ | Si(CH$_3$)$_3$ | OCH$_3$ | OCH$_3$ | CH | |
| 301 | " | " | OCH$_3$ | CH$_3$ | CH | |
| 302 | " | " | OCH$_3$ | Cl | CH | |
| 303 | " | " | CH$_3$ | CH$_3$ | CH | |
| 304 | " | " | OCH$_3$ | OCH$_3$ | N | |

TABLE 1-continued

Compounds of the formula (Ia)

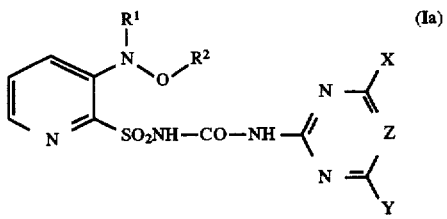

| Ex | R¹ | R² | X | Y | Z | M.p. |
|---|---|---|---|---|---|---|
| 305 | " | " | OCH₃ | CH₃ | N | |
| 306 | " | " | OC₂H₅ | NHCH₃ | N | |
| 307 | CH₃ | H | OCH₃ | OCH₃ | CH | |
| 308 | C₂H₅ | H | OCH₃ | OCH₃ | CH | 149° C. |
| 309 | n-C₃H₇ | H | OCH₃ | OCH₃ | CH | |
| 310 | iso-C₃H₇ | H | OCH₃ | OCH₃ | CH | |
| 311 | cyclo-C₃H₇ | H | OCH₃ | OCH₃ | CH | |
| 312 | n-butyl | H | OCH₃ | OCH₃ | CH | |
| 313 | sec-butyl | H | OCH₃ | OCH₃ | CH | |
| 314 | tert-butyl | H | OCH₃ | OCH₃ | CH | |
| 315 | i-Bu | H | OCH₃ | OCH₃ | CH | |
| 316 | CH₂CF₃ | H | OCH₃ | OCH₃ | CH | |
| 317 | CH₂CF₂H | H | OCH₃ | OCH₃ | CH | |
| 318 | CH₂CH₂F | H | OCH₃ | OCH₃ | CH | |
| 319 | CH₂CH=CH₂ | H | OCH₃ | OCH₃ | CH | |
| 320 | cyclopropyl-methyl | H | OCH₃ | OCH₃ | CH | |
| 321 | CH₂CH₂OCH₃ | H | OCH₃ | OCH₃ | CH | |
| 322 | CH₂CH₂SCH₃ | H | OCH₃ | OCH₃ | CH | |
| 323 | CH₂phenyl | H | OCH₃ | OCH₃ | CH | |
| 324 | CH₂—C≡CH | H | OCH₃ | OCH₃ | CH | |
| 325 | CH₂-cyclohexyl | H | OCH₃ | OCH₃ | CH | |
| 326 | CHO | H | OCH₃ | OCH₃ | CH | |
| 327 | " | H | OCH₃H | CH₃ | CH | |
| 328 | " | H | OCH₃ | Cl | CH | |
| 329 | " | H | CH₃ | CH₃ | CH | |
| 330 | " | H | OCH₃ | CH₃ | N | |
| 331 | " | H | OCH₃ | CH₃ | N | |
| 332 | CHO | H | OC₂H₅ | NHCH₃ | N | |
| 333 | COCH₃ | H | OCH₃ | OCH₃ | CH | 194 |
| 334 | " | H | OCH₃ | CH₃ | CH | |
| 335 | " | H | OCH₃ | Cl | CH | |
| 336 | " | H | CH₃ | CH₃ | CH | |
| 337 | " | H | OCH₃ | OCH₃ | N | |
| 338 | " | H | OCH₃ | CH₃ | N | |
| 339 | " | H | OCH₃ | NHCH₃ | N | |
| 340 | COC₂H₅ | H | OCH₃ | OCH₃ | CH | |
| 341 | COC₃H₇ | H | OCH₃ | OCH₃ | CH | |
| 342 | CO-i-Pr | H | OCH₃ | OCH₃ | CH | |
| 343 | CO-c-Pr | H | OCH₃ | OCH₃ | CH | |
| 344 | CO-c-Bu | H | OCH₃ | OCH₃ | CH | |
| 345 | CO-n-butyl | H | OCH₃ | OCH₃ | CH | |
| 346 | CO-s-Bu | H | OCH₃ | OCH₃ | CH | |
| 347 | CO-t-Bu | H | OCH₃ | OCH₃ | CH | |
| 348 | CO-i-Bu | H | OCH₃ | OCH₃ | CH | |
| 349 | COCH₂OCH₃ | H | OCH₃ | OCH₃ | CH | |
| 350 | COCF₃ | H | OCH₃ | OCH₃ | CH | |
| 351 | COCHCl₂ | H | OCH₃ | OCH₃ | CH | |
| 352 | COCH₂Cl | H | OCH₃ | OCH₃ | CH | |
| 353 | COCCl₃ | H | OCH₃ | OCH₃ | CH | |
| 354 | COCH₂Br | H | OCH₃ | OCH₃ | CH | |
| 355 | COCHF₂ | H | OCH₃ | OCH₃ | CH | |
| 356 | COCH₂F | H | OCH₃ | OCH₃ | CH | |
| 357 | CO₂CH₃ | H | OCH₃ | OCH₃ | CH | |
| 358 | CO₂C₂H₅ | H | OCH₃ | OCH₃ | CH | |
| 359 | CO₂-phenyl | H | OCH₃ | OCH₃ | CH | |
| 360 | CO₂-benzyl | H | OCH₃ | OCH₃ | CH | |
| 361 | CO₂-i-Pr | H | OCH₃ | OCH₃ | CH | |
| 362 | CONHCH₃ | H | OCH₃ | OCH₃ | CH | |
| 363 | CON(CH₃)₂ | H | OCH₃ | OCH₃ | CH | |
| 364 | CONC₂H₅ | H | OCH₃ | OCH₃ | CH | |
| 365 | CON(C₂H₅)₂ | H | OCH₃ | OCH₃ | CH | |

TABLE 1-continued

Compounds of the formula (Ia)

$$\text{(Ia)}$$

| Ex | R¹ | R² | X | Y | Z | M.p. |
|---|---|---|---|---|---|---|
| 366 | CON(pyrrolidinyl) | H | OCH$_3$ | OCH$_3$ | CH | |
| 367 | CH$_3$ | CHO | OCH$_3$ | OCH$_3$ | CH | |
| 368 | " | " | OCH$_3$ | CH$_3$ | CH | |
| 369 | " | " | OCH$_3$ | Cl | CH | |
| 370 | " | " | OCH$_3$ | OCH$_3$ | N | |
| 371 | " | " | OCH$_3$ | CH$_3$ | N | |
| 372 | " | " | OC$_2$H$_5$ | NHCH$_3$ | N | |
| 373 | CH$_3$ | COCH$_3$ | OCH$_3$ | OCH$_3$ | CH | |
| 374 | " | " | OCH$_3$ | CH$_3$ | CH | |
| 375 | " | " | OCH$_3$ | Cl | CH | |
| 376 | " | " | CH$_3$ | CH$_3$ | CH | |
| 377 | " | " | OCH$_3$ | OCH$_3$ | N | |
| 378 | CH$_3$ | COCH$_3$ | OCH$_3$ | CH$_3$ | N | |
| 379 | " | | OC$_2$H$_5$ | NHCH$_3$ | N | |
| 380 | CH$_3$ | COC$_2$H$_5$ | OCH$_3$ | OCH$_3$ | CH | |
| 381 | " | " | OCH$_3$ | CH$_3$ | CH | |
| 382 | " | " | OCH$_3$ | Cl | CH | |
| 383 | " | " | CH$_3$ | CH$_3$ | CH | |
| 384 | " | " | OCH$_3$ | OCH$_3$ | N | |
| 385 | " | " | OCH$_3$ | CH$_3$ | N | |
| 386 | " | " | OC$_2$H$_5$ | NHCH$_3$ | N | |
| 387 | CH$_3$ | COCF$_3$ | OCH$_3$ | OCH$_3$ | CH | |
| 388 | CH$_3$ | COCH$_2$F | OCH$_3$ | OCH$_3$ | CH | |
| 389 | CH$_3$ | CO-n-Pr | OCH$_3$ | OCH$_3$ | CH | |
| 390 | CH$_3$ | CO-i-Pr | OCH$_3$ | OCH$_3$ | CH | |
| 391 | CH$_3$ | CO-c-Pr | OCH$_3$ | OCH$_3$ | CH | |
| 392 | CH$_3$ | CO—Ph | OCH$_3$ | OCH$_3$ | CH | |
| 393 | CH$_3$ | CO-benzyl | OCH$_3$ | OCH$_3$ | CH | |
| 394 | CH$_3$ | CO-n-Bu | OCH$_3$ | OCH$_3$ | CH | |
| 395 | CH$_3$ | CO-s-Bu | OCH$_3$ | OCH$_3$ | CH | |
| 396 | CH$_3$ | CO-i-Bu | OCH$_3$ | OCH$_3$ | CH | |
| 397 | CH$_3$ | CO-t-Bu | OCH$_3$ | OCH$_3$ | CH | |
| 398 | CH$_3$ | COCH$_2$OCH$_3$ | OCH$_3$ | OCH$_3$ | CH | |
| 399 | CH$_3$ | COCH$_2$Br | OCH$_3$ | OCH$_3$ | CH | |
| 400 | CH$_3$ | COCH$_2$CF$_3$ | OCH$_3$ | OCH$_3$ | CH | |
| 401 | CH$_3$ | COCH$_2$Cl | OCH$_2$ | OCH$_2$ | CH | |
| 402 | CH$_3$ | COCHCl$_2$ | OCH$_3$ | OCH$_3$ | CH | |
| 403 | CH$_3$ | CO-c-Bu | OCH$_3$ | OCH$_3$ | CH | |
| 404 | CH$_3$ | CO$_2$CH$_3$ | OCH$_3$ | OCH$_3$ | CH | |
| 405 | " | " | OCH$_3$ | CH$_3$ | CH | |
| 406 | " | " | OCH$_3$ | Cl | CH | |
| 407 | " | " | CH$_3$ | CH$_3$ | CH | |
| 408 | " | " | OCH$_3$ | OCH$_3$ | N | |
| 409 | " | " | OCH$_3$ | CH$_3$ | N | |
| 410 | " | " | OC$_2$H$_5$ | NHCH$_3$ | N | |
| 411 | CH$_3$ | CO$_2$C$_2$H$_5$ | OCH$_3$ | OCH$_3$ | CH | |
| 412 | " | " | OCH$_3$ | CH$_3$ | CH | |
| 413 | " | " | OCH$_3$ | Cl | Cl | |
| 414 | " | " | CH$_3$ | CH$_3$ | CH | |
| 415 | " | " | OCH$_3$ | OCH$_3$ | N | |
| 416 | " | " | OCH$_3$ | CH$_3$ | N | |
| 417 | CH$_3$ | CONHCH$_3$ | OCH$_3$ | OCH$_3$ | CH | |
| 418 | CH$_3$ | CON(CH$_3$)$_2$ | OCH$_3$ | OCH$_3$ | CH | |
| 419 | CH$_3$ | CONHC$_2$H$_5$ | OCH$_3$ | OCH$_3$ | CH | |
| 420 | CH$_3$ | CON(pyrrolidinyl) | OCH$_3$ | OCH$_3$ | CH | |

TABLE 1-continued

Compounds of the formula (Ia)

| Ex | R¹ | R² | X | Y | Z | M.p. |
|---|---|---|---|---|---|---|
| 421 | $C_2H_5$ | CHO | $OCH_3$ | $OCH_3$ | CH | |
| 422 | " | " | $OCH_3$ | $CH_3$ | CH | |
| 423 | " | " | $OCH_3$ | Cl | CH | |
| 424 | $C_2H_5$ | CHO | $OCH_3$ | $OCH_3$ | N | |
| 425 | " | " | $OCH_3$ | $CH_3$ | N | |
| 426 | " | " | $OC_2H_5$ | $NHCH_3$ | N | |
| 427 | $C_2H_5$ | $COCH_3$ | $OCH_3$ | $OCH_3$ | CH | |
| 428 | " | " | $OCCH_3$ | $CH_3$ | CH | |
| 429 | " | " | $OCH_3$ | Cl | CH | |
| 430 | " | " | $CH_3$ | $CH_3$ | CH | |
| 431 | " | " | $OCH_3$ | $OCH_3$ | N | |
| 432 | " | " | $OCH_3$ | $CH_3$ | N | |
| 433 | " | " | $OC_2H_5$ | $NHCH_3$ | N | |
| 434 | $C_2H_5$ | $COC_2H_5$ | $OCH_3$ | $OCH_3$ | CH | |
| 435 | " | " | $OCH_3$ | $CH_3$ | CH | |
| 436 | " | " | $OCH_3$ | Cl | CH | |
| 437 | " | " | $CH_3$ | $CH_3$ | CH | |
| 438 | " | " | $OCH_3$ | $OCH_3$ | N | |
| 439 | " | " | $OCH_3$ | $CH_3$ | N | |
| 440 | " | " | $OC_2H_5$ | $NHCH_3$ | N | |
| 441 | $C_2H_5$ | $COCF_3$ | $OCH_3$ | $OCH_3$ | CH | |
| 442 | $C_2H_5$ | $COCH_2F$ | $OCH_3$ | $OCH_3$ | CH | |
| 443 | $C_2H_5$ | CO-n-Pr | $OCH_3$ | $OCH_3$ | CH | |
| 444 | $C_2H_5$ | CO-i-Pr | $OCH_3$ | $OCH_3$ | CH | |
| 445 | $C_2H_5$ | CO-c-Pr | $OCH_3$ | $OCH_3$ | CH | |
| 446 | $C_2H_5$ | CO—Ph | $OCH_3$ | $OCH_3$ | CH | |
| 447 | $C_2H_5$ | CO-benzyl | $OCH_3$ | $OCH_3$ | CH | |
| 448 | $C_2H_5$ | CO-n-butyl | $OCH_3$ | $OCH_3$ | CH | |
| 449 | $C_2H_5$ | CO-s-butyl | $OCH_3$ | $OCH_3$ | CH | |
| 450 | $C_2H_5$ | CO-i-butyl | $OCH_3$ | $OCH_3$ | CH | |
| 451 | $C_2H_5$ | CO-t-butyl | $OCH_3$ | $OCH_3$ | CH | |
| 452 | $C_2H_5$ | $COCH_2OCH_3$ | $OCH_3$ | $OCH_3$ | CH | |
| 453 | $C_2H_5$ | $COCH_2Br$ | $OCH_3$ | $OCH_3$ | CH | |
| 454 | $C_2H_5$ | $COCH_2CF_3$ | $OCH_3$ | $OCH_3$ | CH | |
| 455 | $C_2H_5$ | $COCH_2Cl$ | $OCH_3$ | $OCH_3$ | CH | |
| 456 | $C_2H_5$ | $COCHCl_2$ | $OCH_3$ | $OCH_3$ | CH | |
| 457 | $C_2H_5$ | CO-c-Bu | $OCH_3$ | $OCH_3$ | CH | |
| 458 | $C_2H_5$ | $CO_2CH_3$ | $OCH_3$ | $OCH_3$ | CH | |
| 459 | " | " | $OCH_3$ | $CH_3$ | CH | |
| 460 | " | " | $OCH_3$ | Cl | CH | |
| 461 | " | " | $CH_3$ | $CH_3$ | CH | |
| 462 | " | " | $OCH_3$ | $OCH_3$ | N | |
| 463 | " | " | $OCH_3$ | $CH_3$ | N | |
| 464 | " | " | $OC_2H_2$ | $NHCH_3$ | N | |
| 465 | $C_2H_5$ | $CO_2C_2H_5$ | $OCH_3$ | $OCH_3$ | CH | |
| 466 | " | " | $OCH_3$ | $CH_3$ | CH | |
| 467 | $C_2H_5$ | $CO_2C_2H_5$ | $OCH_3$ | Cl | Cl | |
| 468 | " | " | $CH_3$ | $CH_3$ | CH | |
| 469 | " | " | $OCH_3$ | $OCH_3$ | N | |
| 470 | $C_2H_5$ | $CO_2C_2H_5$ | $OCH_3$ | $CH_3$ | N | |
| 471 | " | " | $OC_2H_5$ | $NHCH_3$ | N | |
| 472 | $COCH_3$ | $CH_3$ | $OCH_3$ | $OCH_3$ | CH | 169 |
| 473 | " | " | $OCH_3$ | $CH_3$ | CH | |
| 474 | " | " | $OCH_3$ | Cl | CH | |
| 475 | " | " | $CH_3$ | $CH_3$ | CH | |
| 476 | " | " | $OCH_3$ | $OCH_3$ | N | |
| 477 | " | " | $OCH_3$ | $CH_3$ | N | |
| 478 | " | " | $OC_2H_5$ | $NHCH_3$ | N | |
| 479 | CHO | $CH_3$ | $OCH_3$ | $OCH_3$ | CH | |
| 480 | " | " | $OCH_3$ | $CH_3$ | CH | |
| 481 | " | " | $OCH_3$ | Cl | CH | |
| 482 | " | " | $CH_3$ | $CH_3$ | CH | |
| 483 | " | " | $OCH_3$ | $OCH_3$ | N | |

TABLE 1-continued

Compounds of the formula (Ia)

| Ex | R¹ | R² | X | Y | Z | M.p. |
|---|---|---|---|---|---|---|
| 464 | " | " | OCH₃ | CH₃ | N | |
| 485 | " | " | OC₂H₅ | NHCH₃ | N | |
| 486 | COC₂H₅ | CH₃ | OCH₃ | OCH₃ | CH | |
| 487 | " | " | OCH₃ | CH₃ | CH | |
| 488 | " | " | OCH₃ | Cl | CH | |
| 489 | " | " | CH₃ | CH₃ | CH | |
| 490 | " | " | OCH₃ | OCH₃ | N | |
| 491 | COC₂H₅ | CH₃ | OCH₃ | CH₃ | N | |
| 492 | " | " | OC₂H₅ | NHCH₃ | N | |
| 493 | COCH₂OCH₃ | CH₃ | OCH₃ | OCH₃ | CH | |
| 494 | " | " | OCH₃ | CH₃ | CH | |
| 495 | " | " | OCH₃ | Cl | CH | |
| 496 | " | " | CH₃ | CH₃ | CH | |
| 497 | " | " | OCH₃ | OCH₃ | N | |
| 498 | " | " | OCH₃ | CH₃ | N | |
| 499 | " | " | C₂H₅ | NHCH₃ | N | |
| 500 | CO₂CH₃ | CH₃ | OCH₃ | OCH₃ | CH | 154–156 |
| 501 | " | " | OCH₃ | CH₃ | CH | |
| 502 | " | " | OCH₃ | Cl | CH | |
| 503 | " | " | CH₃ | CH₃ | CH | |
| 504 | " | " | OCH₃ | OCH₃ | N | |
| 505 | " | " | OCH₃ | CH₃ | N | |
| 506 | " | " | OC₂H₅ | NHCH₃ | N | |
| 507 | CO₂C₂H₅ | CH₃ | OCH₃ | OCH₃ | CH | |
| 508 | " | " | OCH₃ | CH₃ | CH | |
| 509 | " | " | OCH₃ | Cl | CH | |
| 510 | " | " | CH₃ | CH₃ | CH | |
| 511 | " | " | OCH₃ | OCH₃ | N | |
| 512 | " | " | OCH₃ | CH₃ | N | |
| 513 | " | " | OC₂H₅ | NHCH₃ | N | |
| 514 | CO-phenyl | CH₃ | OCH₃ | OCH₃ | CH | |
| 515 | CO-benzyl | CH₃ | OCH₃ | OCH₃ | CH | |
| 516 | COCH₂F | CH₃ | OCH₃ | OCH₃ | CH | |
| 517 | COCHF₂ | CH₃ | OCH₃ | OCH₃ | CH | |
| 518 | COCF₃ | CH₃ | OCH₃ | OCH₃ | CH | |
| 519 | COCH₂Cl | CH₃ | OCH₃ | OCH₃ | CH | |
| 520 | COCHCl₂ | CH₃ | OCH₃ | OCH₃ | CH | |
| 521 | COCCl₃ | CH₃ | OCH₃ | OCH₃ | CH | |
| 522 | COCH₂CN | CH₃ | OCH₃ | OCH₃ | CH | |
| 523 | COCH₂Br | CH₃ | OCH₃ | OCH₃ | CH | |
| 524 | COCH=CH₂ | CH₃ | OCH₃ | OCH₃ | CH | |
| 525 | COCH₂—CH=CH₂ | CH₃ | OCH₃ | OCH₃ | CH | |
| 526 | CONHCH₃ | CH₃ | OCH₃ | OCH₃ | CH | |
| 527 | CON(CH₃)₂ | CH₃ | OCH₃ | OCH₃ | CH | |
| 528 | CON-pyrrolidinyl | CH₃ | OCH₃ | OCH₃ | CH | |
| 529 | CON-piperidinyl | CH₃ | OCH₃ | OCH₃ | CH | |
| 530 | CON-morpholinyl | CH₃ | OCH₃ | OCH₃ | CH | |
| 531 | CONHC₂H₅ | CH₃ | OCH₃ | OCH₃ | CH | |
| 532 | COCH₃ | C₂H₅ | OCH₃ | OCH₃ | CH | |
| 533 | " | " | OCH₃ | CH₃ | CH | |

TABLE 1-continued

Compounds of the formula (Ia)

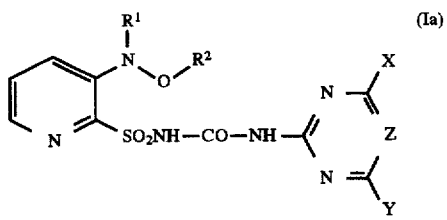

| Ex | R$^1$ | R$^2$ | X | Y | Z | M.p. |
|---|---|---|---|---|---|---|
| 534 | " | " | OCH$_3$ | Cl | CH | |
| 535 | " | " | CH$_3$ | CH$_3$ | CH | |
| 536 | " | " | OCH$_3$ | OCH$_3$ | N | |
| 537 | COCH$_3$ | C$_2$H$_5$ | OCH$_3$ | CH$_3$ | N | |
| 538 | " | " | OC$_2$H$_5$ | NHCH$_2$ | N | |
| 539 | CHO | C$_2$H$_5$ | OCH$_3$ | OCH$_3$ | CN | |
| 540 | " | " | OCH$_3$ | CH$_3$ | CH | |
| 541 | " | " | OCH$_3$ | Cl | CH | |
| 542 | " | " | CH$_3$ | CH$_3$ | CH | |
| 543 | " | " | OCH$_3$ | OCH$_3$ | N | |
| 544 | " | " | OCH$_3$ | CH$_3$ | N | |
| 545 | " | " | OC$_2$H$_5$ | NHCH$_3$ | N | |
| 546 | COC$_2$H$_5$ | C$_2$H$_5$ | OCH$_3$ | OCH$_3$ | CH | |
| 547 | " | " | OCH$_3$ | CH$_3$ | CH | |
| 548 | " | " | OCH$_3$ | Cl | CH | |
| 549 | " | " | CH$_3$ | CH$_3$ | CH | |
| 550 | " | " | OCH$_3$ | OCH$_3$ | N | |
| 551 | " | " | OCH$_3$ | CH$_3$ | N | |
| 552 | " | " | OC$_2$H$_5$ | NHCH$_3$ | N | |
| 553 | CO$_2$CH$_3$ | C$_2$H$_5$ | OCH$_3$ | OCH$_3$ | CH | 172 |
| 554 | " | " | OCH$_3$ | CH$_3$ | CH | |
| 555 | " | " | OCH$_3$ | Cl | CH | |
| 556 | " | " | CH$_3$ | CH$_3$ | CH | |
| 557 | " | " | OCH$_3$ | OCH$_3$ | N | |
| 558 | " | " | OCH$_3$ | CH$_3$ | N | |
| 559 | " | " | OC$_2$H$_5$ | NHCH$_3$ | N | |
| 560 | CO$_2$C$_2$H$_5$ | C$_2$H$_5$ | OCH$_3$ | OCH$_3$ | CH | |
| 561 | CO-phenyl | C$_2$H$_5$ | OCH$_3$ | OCH$_3$ | CH | |
| 562 | CO-benzyl | C$_2$H$_5$ | OCH$_3$ | OCH$_3$ | CH | |
| 563 | COCH$_2$F | C$_2$H$_5$ | OCH$_3$ | OCH$_3$ | CH | |
| 564 | COCHF$_2$ | C$_2$H$_5$ | OCH$_3$ | OCH$_3$ | CH | |
| 565 | COCF$_3$ | C$_2$H$_5$ | OCH$_3$ | OCH$_3$ | CH | |
| 566 | COCH$_2$Cl | C$_2$H$_5$ | OCH$_3$ | OCH$_3$ | CH | |
| 567 | COCHCl$_2$ | C$_2$H$_5$ | OCH$_3$ | OCH$_3$ | CH | |
| 568 | COCCl$_3$ | C$_2$H$_5$ | OCH$_3$ | OCH$_3$ | CH | |
| 569 | COCH$_2$CN | C$_2$H$_5$ | OCH$_3$ | OCH$_3$ | CH | |
| 570 | COCH$_2$Br | C$_2$H$_5$ | OCH$_3$ | OCH$_3$ | CH | |
| 571 | COCH=CH$_2$ | C$_2$H$_5$ | OCH$_3$ | OCH$_3$ | CH | |
| 572 | COCH$_2$CH=CH$_2$ | C$_2$H$_5$ | OCH$_3$ | OCH$_3$ | CH | |
| 573 | CONHCH$_3$ | C$_2$H$_5$ | OCH$_3$ | OCH$_3$ | CH | |
| 574 | CON(CH$_3$)$_2$ | C$_2$H$_5$ | OCH$_3$ | OCH$_3$ | CH | |
| 575 | CON-pyrrolidinyl | C$_2$H$_5$ | OCH$_3$ | OCH$_3$ | CH | |
| 576 | CONHC$_2$H$_5$ | C$_2$H$_5$ | OCH$_3$ | OCH$_3$ | CH | |
| 577 | CONH(C$_2$H$_5$)$_2$ | C$_2$H$_5$ | OCH$_3$ | OCH$_3$ | CH | |
| 578 | COCH$_2$CF$_3$ | C$_2$H$_5$ | OCH$_3$ | OCH$_3$ | CH | |
| 579 | CO-c-Pr | C$_2$H$_5$ | OCH$_3$ | OCH$_3$ | CH | |
| 560 | CO-c-Bu | C$_2$H$_5$ | OCH$_3$ | OCH$_3$ | CH | |
| 581 | CO-c-pentyl | C$_2$H$_5$ | OCH$_3$ | OCH$_3$ | CH | |
| 582 | CO-c-Pr | CH$_3$ | OCH$_3$ | OCH$_3$ | CH | |
| 583 | CO-c-Bu | CH$_3$ | OCH$_3$ | OCH$_3$ | CH | |
| 584 | CO-c-pentyl | CH$_3$ | OCH$_3$ | OCH$_3$ | CH | |
| 585 | H | SO$_2$CH$_3$ | OCH$_3$ | OCH$_3$ | CH | |
| 586 | H | SO$_2$CH$_3$ | CH$_3$ | OCH$_3$ | N | |
| 587 | CH$_3$ | SO$_2$CH$_3$ | OCH$_3$ | OCH$_3$ | CH | |
| 588 | " | " | CH$_3$ | OCH$_3$ | N | |
| 589 | C$_2$H$_5$ | SO$_2$CH$_3$ | OCH$_3$ | OCH$_3$ | CH | |
| 590 | " | " | CH$_3$ | OCH$_3$ | N | |
| 591 | CH$_2$F | SO$_2$CH$_3$ | OCH$_3$ | OCH$_3$ | CH | |

TABLE 1-continued

Compounds of the formula (Ia)

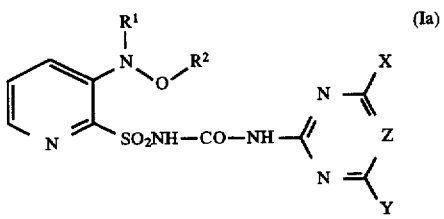

| Ex | R¹ | R² | X | Y | Z | M.p. |
|---|---|---|---|---|---|---|
| 592 | " | " | CH₃ | OCH₃ | N | |
| 593 | CH₂CH₂Cl | SO₂CH₃ | OCH₃ | OCH₃ | CH | |
| 594 | " | " | CH₃ | OCH₃ | N | |
| 595 | CH₂CHCl₂ | " | OCH | OCH₃ | CH | |
| 596 | " | " | CH₃ | OCH₃ | N | |
| 597 | H | SO₂C₂H₅ | OCH₃ | OCH₃ | CH | |
| 598 | " | " | CH₃ | OCH₃ | N | |
| 599 | CH₃ | SO₂C₂H₅ | OCH₃ | OCH₃ | CH | |
| 600 | " | " | CH₃ | OCH₃ | N | |
| 601 | C₂H₅ | SO₂C₂H₅ | OCH₃ | OCH₃ | CH | |
| 602 | " | " | CH₃ | OCH₃ | N | |
| 603 | H | i-Bu | OCH₃ | OCH₃ | CH | |
| 604 | " | " | CH₃ | OCH₃ | N | |
| 605 | CO₂C₂H₅ | SO₂CH₃ | OCH₃ | OCH₃ | CH | |
| 606 | " | " | CH₃ | OCH₃ | N | |
| 607 | CO₂CH₃ | SO₂C₂H₅ | OCH₃ | OCH₃ | CH | |
| 608 | " | " | CH₃ | OCH₃ | N | |

TABLE 2

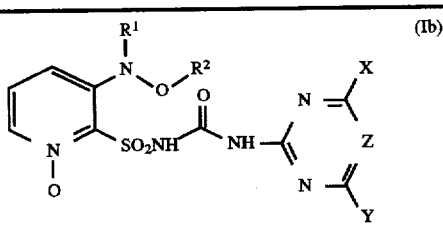

| Ex. | R¹ | R² | X | Y | Z | M.p. |
|---|---|---|---|---|---|---|
| 609 | H | H | OCH₃ | OCH₃ | CH | |
| 610 | H | CH₃ | OCH₃ | OCH₃ | CH | |
| 611 | H | CHF₂ | OCH₃ | OCH₃ | CH | |
| 612 | H | C₂H₅ | OCH₃ | OCH₃ | CH | |
| 613 | H | i-Bu | OCH₃ | OCH₃ | CH | |
| 614 | H | n-C₃H₇ | OCH₃ | OCH₃ | CH | |
| 615 | CH₃ | CH₃ | OCH₃ | OCH₃ | CH | |
| 616 | CH₃ | C₂H₅ | OCH₃ | OCH₃ | CH | |
| 617 | CH₃ | CHF₂ | OCH₃ | OCH₃ | CH | |
| 618 | CH₃ | H | OCH₃ | OCH₃ | CH | |
| 619 | C₂H₅ | H | OCH₃ | OCH₃ | CH | |
| 620 | C₂H₅ | CH₃ | OCH₃ | OCH₃ | CH | |
| 621 | C₂H₅ | C₂H₅ | OCH₃ | OCH₃ | CH | |
| 622 | H | COCH₃ | OCH₃ | OCH₃ | CH | |
| 623 | H | CO₂CH₃ | OCH₃ | OCH₃ | CH | |
| 624 | H | COC₂H₅ | OCH₃ | OCH₃ | CH | |
| 625 | H | COCH₂Cl | OCH₃ | OCH₃ | CH | |
| 626 | CH₃ | COCH₃ | OCH₃ | OCH₃ | CH | |
| 627 | CH₃ | CO₂CH₃ | OCH₃ | OCH₃ | CH | |
| 628 | CH₃ | COCH₂Cl | OCH₃ | OCH₃ | CH | |
| 629 | C₂H₅ | COCH₃ | OCH₃ | OCH₃ | CH | |
| 630 | C₂H₅ | COCH₂Cl | OCH₃ | OCH₃ | CH | |
| 631 | C₂H₅ | COCH₂Cl | OCH₃ | OCH₃ | CH | |
| 632 | CHO | CH₃ | OCH₃ | OCH₃ | CH | |
| 633 | COCH₃ | CH₃ | OCH₃ | OCH₃ | CH | |
| 634 | CO₂CH₃ | CH₃ | OCH₃ | OCH₃ | CH | |
| 635 | CO₂C₂H₅ | CH₃ | OCH₃ | OCH₃ | CH | |

TABLE 3

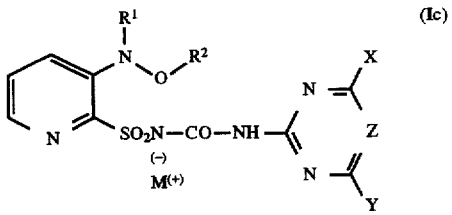

| Ex. | R¹ | R² | X | Y | Z | M⁺ | M.p. |
|---|---|---|---|---|---|---|---|
| 636 | H | H | OCH₃ | OCH₃ | CH | Na⁺ | |
| 637 | H | H | OCH₃ | OCH₃ | CH | Li⁺ | |
| 638 | H | H | OCH₃ | OCH₃ | CH | NH₄⁺ | |
| 639 | CH₃ | CH₃ | OCH₃ | OCH₃ | CH | Na⁺ | 183–189 |
| 640 | CH₃ | CH₃ | OCH₃ | OCH₃ | CH | Li⁺ | |
| 641 | C₂H₅ | CH₃ | OCH₃ | OCH₃ | CH | Na⁺ | |
| 642 | CH₃ | COCH₃ | OCH₃ | OCH₃ | CH | Na⁺ | |
| 643 | CHO | CH₃ | OCH₃ | OCH₃ | CH | Na⁺ | |
| 644 | COCH₃ | CH₃ | OCH₃ | OCH₃ | CH | Na⁺ | |
| 645 | CO₂CH₃ | CH₃ | OCH₃ | OCH₃ | CH | Li⁽⁺⁾ | |
| 646 | CH₂CF₃ | CH₃ | OCH₃ | OCH₃ | CH | Na⁺ | |
| 647 | CH₃ | CO₂CH₃ | OCH₃ | OCH₃ | CH | Na⁺ | |
| 647a | C₂H₅ | C₂H₅ | OCH₃ | OCH₃ | CH | Na⁺ | 199–200 |

TABLE 4

Compounds of the formula (IIa) in the context of formulae (II) and (VIII)

$$\underset{N}{(R^3)_n} \diagdown \overset{\overset{R^1}{|}}{\underset{SO_2NH-R^7}{N-O-R^2}} \quad (IIa)$$

| Ex. | R¹ | R² | R⁷ | (R³)ₙ | M.p. |
|---|---|---|---|---|---|
| 648 | H | H | H | — | oil |
| 649 | H | H | tert-butyl | — | 125° C. |
| 650 | H | CH₃ | H | — | 149° C. |
| 651 | H | CH₃ | tert-butyl | — | 128° C. |
| 652 | H | C₂H₅ | H | — | 112° C. |
| 653 | H | C₂H₅ | tert-butyl | — | 107° C. |
| 654 | H | nC₃H₇ | H | — | 91–92° C. |
| 655 | H | n-C₃H₇ | tert-butyl | — | oil |
| 656 | H | i-C₃H₇ | H | — | oil |
| 657 | H | i-C₃H₇ | tert-butyl | — | oil |
| 658 | H | i-Bu | H | — | oil |
| 659 | H | i-Bu | tert-butyl | — | oil |
| 660 | H | Si(CH₃)₃ | H | — | |
| 661 | H | Si(CH₃)₃ | tert-butyl | — | |
| 662 | H | COCH₃ | H | — | 121° C. |
| 663 | H | COCH₃ | tert-butyl | — | 147–149° C. |
| 664 | H | CHO | H | — | |
| 665 | H | CHO | tert-butyl | — | |
| 666 | H | COC₂H₅ | H | — | 104–106° C. |
| 667 | H | COC₂H₅ | tert-butyl | — | 115–116° C. |
| 668 | H | CO-i-Pr | H | — | oil |
| 669 | H | CO-i-Pr | tert-butyl | — | 100° C. |
| 670 | H | CO-t-butyl | H | — | oil |
| 671 | H | CO-tert-butyl | tert-butyl | — | 122–124° C. |
| 672 | H | CO-benzyl | H | — | 111–113° C. |
| 673 | H | CO-benzyl | tert-butyl | — | 106–107° C. |
| 674 | H | COCH₂OCH₃ | H | — | 116° C. |
| 675 | H | COCH₂OCH₃ | tert-butyl | — | 86–87° C. |
| 676 | H | CO-n-C₅H₁₁ | H | — | oil |
| 677 | H | CO-n-C₅H₁₁ | tert-butyl | — | 72–73° C. |
| 678 | H | CO-cyclopropyl | H | — | 116–121° C. |
| 779 | H | CO-cyclopropyl | tert-butyl | — | oil |
| 780 | H | CO₂CH₃ | H | — | 123–126° C. |
| 781 | H | CO₂CH₃ | tert-butyl | — | 105–107° C. |
| 782 | H | CO₂C₂H₅ | H | — | 108–111° C. |
| 783 | H | CO₂C₂H₅ | tert-butyl | — | 93–95° C. |
| 784 | CH₃ | CH₃ | H | — | 135° C. |
| 785 | CH₃ | CH₃ | tert-butyl | — | 120° C. (decomp.) |
| 786 | CH₃ | C₂H₅ | H | — | |
| 787 | CH₃ | C₂H₅ | tert-butyl | — | |
| 788 | CH₃ | C₃H₇ | H | — | |
| 789 | CH₃ | C₃H₇ | tert-butyl | — | |
| 790 | C₂H₅ | CH₃ | H | — | |
| 791 | C₂H₅ | CH₃ | tert-butyl | — | |
| 792 | C₂H₅ | C₂H₅ | H | — | 169° C. |
| 793 | C₂H₅ | C₂H₅ | tert-butyl | — | oil |
| 794 | C₂H₅ | C₃H₇ | H | — | |
| 795 | C₂H₅ | C₃H₇ | tert-butyl | — | |
| 796 | CHO | H | H | — | |
| 797 | CHO | H | tert-butyl | — | |
| 798 | COCH₃ | H | H | — | oil |
| 799 | COCH₃ | H | tert-butyl | — | 135° C. |
| 800 | COC₂H₅ | H | H | — | |
| 801 | COC₂H₅ | H | tert-butyl | — | |
| 802 | CO₂CH₃ | H | H | — | 120–122° C. |
| 803 | " | H | tert-butyl | — | 157° C. (decomp.) |
| 804 | CO₂H₅ | H | H | — | |
| 805 | " | H | tert-butyl | — | |
| 806 | — | — | — | — | — |
| 807 | — | — | — | — | — |
| 808 | CHO | CHO | H | — | |
| 809 | " | " | tert-butyl | — | |
| 810 | COCH₃ | COCH₃ | H | — | oil |
| 811 | " | " | tert-butyl | — | 137° C. (decomp.) |
| 812 | COC₂H₅ | COC₂H₅ | H | — | |
| 813 | " | " | tert-butyl | — | |
| 814 | H | CON(CH₃)₂ | H | — | |
| 815 | " | " | tert-butyl | — | 98–100° C. |
| 816 | H | CON(C₂H₅)₂ | H | — | |
| 817 | " | " | tert-butyl | — | |
| 818 | CON(CH₃)₂ | H | H | — | |
| 819 | " | " | tert-butyl | — | |
| 820 | CH₃ | CHO | H | — | |
| 821 | " | " | tert-butyl | — | |
| 822 | CH₃ | CH₃ | H | — | |
| 823 | " | " | tert-butyl | — | |
| 824 | CH₃ | COC₂H₅ | H | — | |
| 825 | " | " | tert-butyl | — | |
| 826 | C₂H₅ | COCH₃ | H | — | oil |
| 827 | " | " | tert-butyl | — | 127–129° C. |
| 828 | CHO | CH₃ | H | — | 121° C. |
| 829 | " | " | tert-butyl | — | 152° C. |
| 830 | COCH₃ | CH₃ | H | — | 168–170° C. |
| 831 | " | " | tert-butyl | — | oil |
| 832 | CO₂CH₃ | CH₃ | H | — | 142° C. |
| 833 | " | " | tert-butyl | — | 159° C. |
| 834 | COCH₃ | C₂H₅ | H | — | 149° C. |
| 835 | " | " | tert-butyl | — | oil |
| 836 | CO₂CH₃ | C₂H₅ | H | — | |
| 837 | " | " | tert-butyl | — | |
| 838 | CO₂CH₃ | CH₃ | H | — | |
| 839 | " | " | tert-Butyl | — | |
| 840 | — | — | — | — | — |
| 841 | — | — | — | — | — |
| 842 | — | — | — | — | — |
| 843 | — | — | — | — | — |
| 844 | CH₃ | SO₂CH₃ | H | — | |
| 845 | " | " | tert-butyl | — | |
| 846 | C₂H₅ | SO₂CH₃ | H | — | |
| 847 | " | " | tert-butyl | — | |
| 848 | H | SO₂CH₃ | H | — | |
| 849 | " | " | tert-butyl | — | |
| 850 | CH₃ | H | H | — | oil |
| 851 | " | " | tert-butyl | — | 172–177° C. |
| 852 | C₂H₅ | H | H | — | 133–135° C. |
| 853 | " | " | tert-butyl | — | 154° C. |
| 854 | C₃H₇ | H | H | — | |
| 855 | " | " | tert-butyl | — | |
| 856 | CHO | C₂H₅ | H | — | oil |
| 857 | " | " | tert-butyl | — | oil |
| 858 | H | CO phenyl | H | — | 139° C. |
| 859 | " | " | tert-butyl | — | 171–173° C. |
| 860 | CH₃ | SO₂CH₃ | H | — | |
| 861 | " | " | tert-butyl | — | |
| 862 | C₂H₅ | SO₂CH₃ | H | — | |
| 863 | " | " | tert-butyl | — | |
| 864 | CH₃ | SO₂C₂H₅ | H | — | |
| 865 | " | " | tert-butyl | — | |
| 866 | H | SO₂C₂H₅ | H | — | |
| 867 | " | " | tert-butyl | — | |

TABLE 5

Compounds of the formula (Ie)

$$\text{R}^3 \underset{N}{\overset{R^1}{\underset{\underset{SO_2-NH-CO-NH}{|}}{\bigg\langle}}} \text{N} \overset{OCH_3}{\underset{OCH_3}{\bigg\langle}} \text{N}$$ (Ie)

| Example | R¹ | R² | R³ |
|---|---|---|---|
| 5-1 | H | CH₃ | 6-Cl |
| 5-2 | " | " | 5-Cl |
| 5-3 | " | " | 6-F |
| 5-4 | " | " | 5-F |
| 5-5 | " | " | 6-CH₃ |
| 5-6 | " | " | 5-CH₃ |
| 5-7 | H | C₂H₅ | 6-Cl |
| 5-8 | " | " | 6-CH₃ |
| 5-9 | " | " | 6-F |
| 5-10 | " | " | 5-Cl |
| 5-11 | " | " | 5-CH₃ |
| 5-12 | " | " | 5-F |
| 5-13 | CH₃ | CH₃ | 6-Cl |
| 5-14 | " | " | 6-F |
| 5-15 | " | " | 6-CH₃ |
| 5-16 | " | " | 5-Cl |
| 5-17 | CH₃ | CH₃ | 5-F |
| 5-18 | " | " | 5-CH₃ |
| 5-19 | CH₃ | H | 6-Cl |
| 5-20 | " | " | 6-F |
| 5-21 | " | " | 6-CH₃ |
| 5-22 | " | " | 5-F |
| 5-23 | " | " | 5-CH₃ |
| 5-24 | C₂H₅ | H | 6-CH₃ |
| 5-25 | " | " | 6-F |
| 5-26 | " | " | 5-CH₃ |
| 5-27 | " | " | 5-F |
| 5-28 | C₂H₅ | COCH₃ | 6-Cl |
| 5-29 | " | " | 6-F |
| 5-30 | " | " | 6-CH₃ |
| 5-31 | " | " | 5-F |
| 5-32 | " | " | 5-CONH₂ |
| 5-33 | CH₃ | COCH₃ | 6-Cl |
| 5-34 | " | " | 6-F |
| 5-35 | " | " | 5-CH₃ |
| 5-36 | " | " | 5-F |
| 5-37 | C₂H₅ | OSO₂CH₃ | 6-Cl |
| 5-38 | " | " | 6-F |
| 5-38 | C₂H₅ | OSO₂CH₃ | 6-CH₃ |
| 5-39 | " | " | 5-CH₃ |
| 5-40 | " | " | 5-F |
| 5-41 | " | " | 5-N(CH₃)₂ |
| 5-42 | COCH₃ | CH₃ | 6-Cl |
| 5-43 | " | " | 6-F |
| 5-44 | " | " | 6-CH₃ |
| 5-45 | " | " | 5-N(CH₃)₂ |
| 5-46 | H | CH₃ | 6-CH₃ |
| 5-47 | " | " | 5-CH₃ |
| 5-48 | " | " | 6-F |
| 5-49 | " | " | 5-F |
| 5-50 | " | " | 6-Cl |
| 5-51 | " | " | 5-Cl |
| 5-52 | " | " | 5-CON(CH₃)₂ |
| 5-53 | H | C₂H₅ | 6-CH₃ |
| 5-54 | " | " | 5-CH₃ |
| 5-55 | " | " | 6-F |
| 5-56 | " | " | 5-F |

B. FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignin sulfonate and 1 part by weight of sodium oleylmethyltaurinate as wetting agent and dispersant and grinding the mixture in a pinned-disc mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255° to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of oxethylated nonylphenol as emulsifier e) water-dispersible granules are obtained by mixing 75 parts by weight of a compound of the formula (I),
10 parts by weight of calcium lignin sulfonate,
5 parts by weight of sodium lauryl sulfate,
3 parts by weight of polyvinyl alcohol and
7 parts by weight of kaolin, grinding the mixture in a pinned-disc mill and granulating the powder in a fluidized bed by spraying on water as the granulation liquid.

f) Water-dispersible granules are also obtained by homogenizing and precomminuting 25 parts by weight of a compound of the formula (I),
5 parts by weight of sodium 2,2'-dinaphthyl-methane-6,6'-disulfonate,
2 parts by weight of sodium oleylmethyltaurinate,
1 part by weight of polyvinyl alcohol,
17 parts by weight of calcium carbonate and
50 parts by weight of water in a colloid mill, subsequently grinding the mixture in a bead mill, and atomizing and drying the resulting suspension in a spray tower by means of a single-substance nozzle.

C. BIOLOGICAL EXAMPLES

1. Pre-emergence Effect on Weeds

Seeds or rhizome pieces of monocotyledon and dicotyledon weed plants were placed in sandy loam soil in plastic pots and covered with soil. The compounds according to the invention, which had been formulated in the form of wettable powders or emulsion concentrates, were then applied to the surface of the soil cover in the form of aqueous suspensions or emulsions at an application rate of 600 to 800 l of water/ha (converted) at various dosage rates. After the treatment, the pots were placed in a greenhouse and kept under good growth conditions for the weeds. After the test plants had emerged after a test period of 3 to 4 weeks, the damage to the plants or the negative effect on the emergence was scored visually by comparison with untreated controls. As shown by the test results, the compounds according to the invention have a good herbicidal pre-emergence activity against a broad spectrum of grass weeds and broad-leaved weeds. The compounds of the above examples (see Tables 1–3, 5) 1, 8, 15, 23, 29, 36, 43, 56, 69, 76, 90, 97, 111, 118, 125, 198, 333, 472, 500, 553, 639 and 647a, for example, have a very good herbicidal activity against harmful plants such as *Sinapis alba, Chrysanthemum segetum, Avena sativa, Stellaria media, Echinochloa crus-galli, Lolium multiflorum, Setaria spp., Abutilon theophrasti, Amaranthus retroflexus* and *Panicum miliaceum* when used pre-emergence at an application rate of 0.3 kg and less of active ingredient per hectare.

2. Post-emergence Effect on Weeds

Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage. The compounds according to the invention, which had been formulated as wettable powders or as emulsion concentrates, were sprayed at various dosage rates onto the green parts of the plants at an application rate of 600 to 800 l of water/ha (converted), and, after the test plants had remained in the greenhouse for approximately 3 to 4 weeks under ideal growth conditions, the effect of the preparations was scored visually by comparison with untreated controls. The compositions according to the invention also have a good herbicidal post-emergence activity against a broad spectrum of economically important grass weeds and broad-leaved weeds. The compounds of the abovementioned examples (see Tables 1–3, 5) 1, 8, 15, 23, 29, 36, 43, 56, 69, 76, 90, 97, 111, 118, 125, 198, 333, 472, 500, 553, 639 and 647a, for example, have a very good herbicidal activity against harmful plants such as *Sinapis alba, Stellaria media, Echinochloa curs-galli, Lolium multiflorum, Chrysanthemum segetum, Setaria spp., Abutilon theophrasti, Amaranthus retroflexus, Panicum miliaceum* and *Avena sativa* when used post-emergence at an application rate of 0.3 kg and less of active ingredient per hectare.

We claim:

1. A compound of the formula (I) or a salt thereof

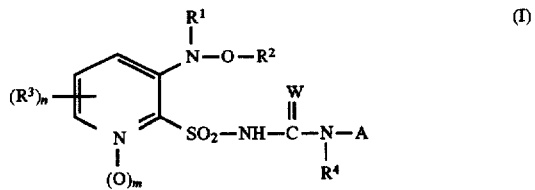

in which $R^1$ is H, $(C_1-C_6)$alkyl which is unsubstituted or substituted by one or more radicals selected from the group consisting of halogen, nitro, $(C_1-C_4)$alkoxy, $(C_3-C_6)$cycloalkyl, cyano, aryl and substituted aryl, $(C_3-C_6)$cycloalkyl which is unsubstituted or substituted by one or more radicals selected from the group consisting of halogen, $(C_1-C_4)$alkyl and $(C_1-C_4)$alkoxy, or $(C_2-C_6)$alkenyl or $(C_2-C_6)$alkynyl, each of the two last-mentioned radicals being unsubstituted or substituted by one or more radicals selected from the group consisting of halogen, $(C_1-C_4)$alkoxy and $(C_3-C_6)$cycloalkyl, or is aryl, substituted aryl, or an acyl radical of the formula

—CO—R* in which

R* is H, $(C_1-C_6)$alkyl, $(C_2-C_6)$alkenyl or $(C_2-C_6)$alkynyl, each of the three last-mentioned radicals being unsubstituted or substituted by one or more radicals selected from the group consisting of halogen, $(C_1-C_4)$alkoxy, $(C_1-C_4)$alkylthio, $(C_1-C_4)$alkylsulfinyl, $(C_1-C_4)$alkylsulfonyl, nitro, cyano, thiocyanato, aryl, and substituted aryl, or is $(C_1-C_4)$alkoxy, $(C_2-C_4)$alkenyloxy, $(C_2-C_4)$alkynyloxy or $(C_1-C_4)$alkylthio, each of the last-mentioned four radicals being unsubstituted or substituted by one or more radicals selected from the group consisting of halogen, $(C_1-C_4)$alkoxy, $(C_1-C_4)$alkylthio, aryl and substituted aryl, or is $(C_3-C_6)$cycloalkyl or $(C_3-C_6)$cycloalkoxy, each of the lastmentioned two radicals being unsubstituted or substituted by one or more radicals selected from the group consisting of $(C_1-C_4)$alkyl, $(C_1-C_4)$alkoxy, $(C_1-C_4)$alkylthio, $(C_1-C_4)$haloalkyl, and halogen, or is a radical of the formula $NR^aR^b$, $R^2$ is H, $(C_1-C_6)$alkyl which is unsubstituted or substituted by one or more radicals selected from the group consisting of halogen, nitro, $(C_1-C_4)$alkoxy, $(C_3-C_6)$cycloalkyl, aryl and substituted aryl, or $(C_3-C_6)$cycloalkyl which is unsubstituted or substituted by one or more radicals selected from the group consisting of halogen, $(C_1-C_4)$alkyl, $(C_1-C_4)$alkoxy, $(C_1C_4)$haloalkyl, aryl and substituted aryl, or $(C_2-C_6)$alkenyl or $(C_2-C_6)$alkynyl, each of the last-mentioned two radicals being unsubstituted or substituted by one or more radicals selected from the group consisting of $(C_1-C_4)$alkoxy, $(C_1-C_4)$haloalkyl, $(C_3-C_6)$cycloalkyl and halogen, or aryl, substituted aryl or a radical of the formula R'R"R'"Si, in which R', R" and R'" independently of one another are $(C_1-C_4)$alkyl, or an acyl radical of the formula

—CO—R** in which

R** is H, $(C_1-C_6)$alkyl, $(C_2-C_6)$alkenyl or $(C_2-C_6)$alkynyl, each of the three last-mentioned radicals being unsubstituted or substituted by one or more radicals selected from the group consisting of halogen, $(C_1-C_4)$alkoxy, $(C_1-C_4)$alkylthio, $(C_1-C_4)$alkylsulfinyl, $(C_1-C_4)$alkylsulfonyl, nitro, cyano, thiocyanato, aryl, and substituted aryl, or is $(C_1-C_4)$alkoxy, $(C_2-C_4)$alkenyloxy or $(C_2-C_4)$alkynyloxy, each of the last-mentioned three radicals being unsubstituted or substituted by one or more radicals selected from the group consisting of halogen, $(C_1-C_4)$alkoxy, $(C_1-C_4)$alkylthio, aryl and substituted aryl, or is $(C_3-C_6)$cycloalkyl or $(C_3-C_6)$cycloalkoxy, each of the last-mentioned two radicals being unsubstituted or substituted by one or more radicals selected from the group consisting of halogen, $(C_1-C_4)$alkyl, $(C_1-C_4)$alkoxy, $(C_1-C_4)$alkylthio and $(C_1-C_4)$haloalkyl, or is a radical of the formula $NR^cR^d$, $R^3$ is $(C_1-C_4)$alkyl, $(C_1-C_3)$haloalkyl, halogen, $NO_2$, CN, $(C_1-C_3)$alkoxy, $(C_1-C_3)$haloalkoxy, $(C_1-C_3)$alkylthio, $(C_1-C_3)$alkoxy-$(C_1-C_3)$alkyl, [$(C_1-C_3)$alkoxy]-carbonyl, $(C_1-C_3)$alkylamino, di[$(C_1-C_3)$alkyl]-amino, $(C_1-C_3)$-alkylsulfinyl, $(C_1-C_3)$alkylsulfonyl, $SO_2NR^eR^f$ or $C(O)NR^gR^h$, $R^a$, $R^b$, $R^c$, $R^d$, $R^e$, $R^f$, $R^g$ and $R^h$ independently of one another are H, $(C_1-C_4)$alkyl, $(C_3-C_6)$alkenyl, $(C_3-C_6)$alkynyl, [$(C_1-C_4)$alkyl]-carbonyl, arylcarbonyl which is substituted in the aryl radical or substituted by one or more radicals selected from the group consisting of halogen, $(C_1-C_4)$alkyl and $(C_1-C_4)$alkoxy, or the pairs $R^a$ and $R^b$, $R^c$ and $R^d$, $R^e$ and $R^f$ or $R^g$ and $R^h$ together

45 with the nitrogen atom linking them are a heterocyclic saturated or unsaturated ring having 3 to 7 ring atoms, which can contain, besides the nitrogen atom, 1 or 2 further heteroatoms selected from the group consisting of N, O and S at the oxidation levels which are possible and which is unsubstituted or substituted, $R^4$ is H or $(C_1-C_4)$alkyl, m is 0 or 1, n is 0, 1 or 2, A is a radical of the formula

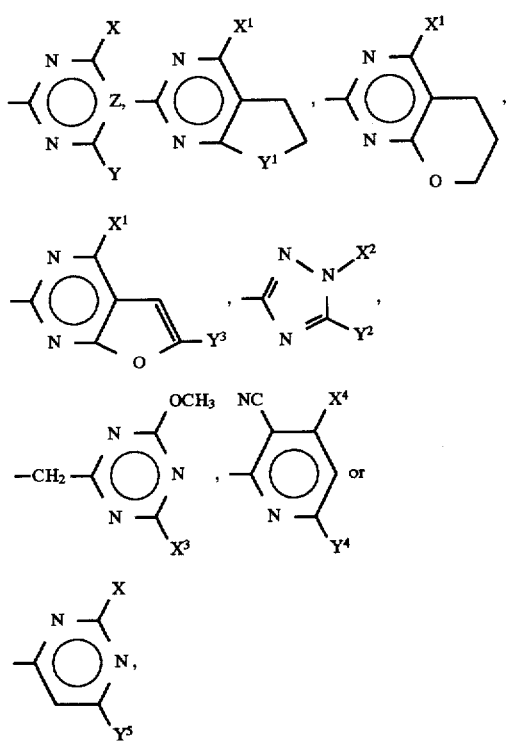

X and Y independently of one another are H, halogen, $(C_1-C_3)$alkyl, $(C_1-C_3)$alkoxy or $(C_1-C_3)$alkylthio, with the abovementioned alkyl-containing radicals being unsubstituted or mono- or polysubstituted by halogen or mono- or disubstituted by $(C_1-C_3)$alkoxy or $(C_1-C_3)$alkylthio, or are a radical of the formula $NR^5R^6$, $(C_3-C_6)$-cycloalkyl, $(C_2-C_4)$alkenyl, $(C_2-C_4)$alkynyl, $(C_3-C_4)$alkenyloxy or $(C_3-C_4)$alkynyloxy, $R^5$ and $R^6$ independently of one another are H, $(C_1-C_3)$alkyl or $(C_3-C_4)$alkenyl, W is O or S, Z is CH or N, $X^1$ is $CH_3$, $OCH_3$, $OC_2H_5$ or $OCF_2H$, $Y^1$ is —O— or —$CH_2$—, $X^2$ is $CH_3$, $C_2H_5$ or $CH_2CF_3$, $Y^2$ is $OCH_3$, $OC_2H_5$, $SCH_3$, $SC_2H_5$, $CH_3$ or $C_2H_5$, $X^3$ is $CH_3$ or $OCH_3$, $Y^3$ is H or $CH_3$, $X^4$ is $CH_3$, $OCH_3$, $OC_2H_5$, $CH_2OCH_3$ or Cl, $Y^4$ is $CH_3$, $OCH_3$, $OC_2H_5$ or Cl and $Y^5$ is $CH_3$, $C_2H_5$, $OCH_3$ or Cl.

2. A compound or a salt thereof as claimed in claim 1, wherein $R^1$ is H, $(C_1-C_4)$alkyl which is unsubstituted or substituted by one or more radicals selected from the group

46 consisting of halogen, $(C_1-C_4)$alkoxy, $(C_3-C_6)$cycloalkyl, or phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy and $(C_1-C_4)$alkylthio, or $(C_3-C_6)$cycloalkyl, $(C_2-C_4)$alkenyl, $(C_2-C_4)$haloalkenyl, $(C_2-C_6)$alkynyl, phenyl, substituted phenyl or a radical of the formula

—CO—R* in which

R* is H, $(C_1-C_4)$alkyl, $(C_2-C_4)$alkenyl or $(C_2-C_4)$alkynyl, each of the three last-mentioned radicals being unsubstituted or substituted by one or more radicals selected from the group consisting of halogen, $(C_1-C_4)$alkoxy, $(C_1-C_4)$alkylsulfonyl, phenyl, and substituted phenyl, or is $(C_1-C_4)$alkoxy which is unsubstituted or substituted by one or more radicals selected from the group consisting of halogen, $(C_1-C_4)$alkoxy, $(C_1-C_4)$alkylthio, phenyl and substituted aryl, or $(C_3-C_6)$cycloalkyl or $(C_3-C_6)$cycloalkoxy, each of the last-mentioned two radicals being unsubstituted or substituted by one or more radicals selected from the group consisting of $(C_1-C_4)$alkyl, $(C_1-C_2)$alkoxy and halogen; or is a radical of the formula $NR^aR^b$.

3. A compound or a salt thereof as claimed in claim 1, wherein $R^1$ is H, $(C_1-C_4)$alkyl which is unsubstituted or substituted by 1 to 3 radicals selected from the group consisting of halogen or by $(C_1-C_2)$alkoxy or $(C_3-C_5)$cycloalkyl, or is a radical of the formula —CO—R* in which R* is H, $(C_1-C_4)$alkyl which is unsubstituted or substituted by one or more halogen atoms or by $(C_1-C_2)$alkoxy, or $(C_2-C_4)$alkenyl, $(C_2-C_3)$alkynyl, $(C_3-C_5)$cycloalkyl, $(C_1-C_4)$alkoxy which is unsubstituted or substituted by one or more halogen atoms or by phenyl, or a radical of the formula $NR^aR^b$, in which $R^a$ and $R^b$ independently of one another are H or $(C_1-C_4)$alkyl, $R^2$ is H, $(C_1-C_4)$alkyl which is unsubstituted or substituted by one or more radicals selected from the group consisting of halogen, $(C_1-C_4)$alkoxy, $(C_3-C_6)$cycloalkyl, phenyl and substituted phenyl, or $(C_3-C_6)$cycloalkyl which is unsubstituted or substituted by one or more radicals selected from the group consisting of halogen, $(C_1-C_4)$alkyl, $(C_1-C_4)$alkoxy or $(C_1-C_4)$haloalkyl, or $(C_2-C_4)$alkenyl or $(C_2-C_4)$alkynyl, each of the last-mentioned two radicals being unsubstituted or substituted by one or more radicals selected from the group consisting of $(C_1-C_4)$alkoxy, $(C_1-C_4)$haloalkyl and halogen, or is phenyl, substituted phenyl or a radical of the formula R'R"R'"Si, in which R', R" and R'" independently of one another are $(C_1-C_4)$alkyl, or an acyl radical of the formula

—CO—R** in which

R** is H, $(C_1-C_4)$alkyl, $(C_2-C_4)$alkenyl or $(C_2-C_4)$alkynyl, each of the three last-mentioned radicals being unsubstituted or substituted by one or more radicals selected from the group consisting of halogen, $(C_1-C_4)$alkoxy, $(C_1-C_4)$alkylsulfonyl, phenyl and substituted phenyl, or is $(C_1-C_4)$alkoxy, $(C_3-C_4)$alkenyloxy or $(C_3-C_4)$alkynyloxy, each of the last-mentioned three radicals being unsubstituted or substituted by one or more radicals selected from the group consisting of halogen, $(C_1-C_4)$alkoxy, $(C_1-C_4)$alkylthio, phenyl and substituted phenyl, or is $(C_3-C_6)$cycloalkyl or $(C_3-C_6)$cycloalkoxy, each of the last-mentioned two radicals being unsubstituted or substituted by one or more radicals selected from the group consisting of halogen, $(C_1-C_4)$alkyl, $(C_1-C_4)$alkoxy and $(C_1-C_4)$haloalkyl, or a radical of the formula $NR^cR^d$, $R^3$ is $(C_1-C_3)$alkyl, $(C_1-C_3)$haloalkyl, halogen, $NO_2$, $(C_1-C_3)$alkoxy, $(C_1-C_3)$haloalkoxy, $(C_1-C_2)$alkoxy-$(C_1-C_2)$alkyl, acetyl, propionyl, $(C_1-C_2)$-alkylamino, di[$(C_1-C_2)$alkyl]amino, $(C_1-C_3)$-alkylsulfonyl, $SO_2NR^eR^f$ or $C(O)NR^gR^h$.

4. A compound or a salt thereof as claimed in claim 1, wherein $R^1$ is H, $(C_1-C_4)$alkyl, $(C_1-C_4)$haloalkyl or [$(C_1-C_2)$alkoxy]-$(C_1-C_2)$alkyl, or a radical of the formula —CO—R* in which R* is H, $(C_1-C_4)$alkyl, halo-$(C_1-C_4)$alkyl, $(C_2-C_4)$alkenyl, $(C_2-C_4)$alkynyl, $(C_1-C_4)$alkoxy, [$(C_1-C_2)$alkoxy]-$(C_1-C_2)$alkyl, $(C_3-C_5)$cycloalkyl or a radical of the formula $NR^aR^b$ in which $R^a$ and $R^b$ independently of one another are H or $(C_1-C_4)$alkyl, $R^2$ is H, $(C_1-C_4)$alkyl, $(C_1-C_4)$haloalkyl, [$(C_1-C_2)$alkoxy]-$(C_1-C_2)$alkyl or a radical of the formula —CO—R in which R is H, $(C_1-C_4)$alkyl, $(C_1-C_4)$haloalkyl, $(C_3-C_4)$alkenyl, $(C_3-C_4)$alkynyl, $(C_1-C_4)$alkoxy, [$(C_1-C_2)$alkoxy]-$(C_1-C_2)$alkyl, $(C_3-C_5)$cycloalkyl or a radical of the formula $NR^cR^d$, in which $R^c$ and $R^d$ independently of one another are H or $(C_1-C_4)$alkyl, $R^3$ is $(C_1-C_4)$alkyl, halogen, nitro or $(C_1-C_4)$alkoxy, n is 0 or 1 and A is a radical of the formula

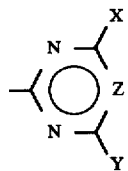

in which one of the radicals X and Y is $(C_1-C_3)$alkyl, $(C_1-C_3)$alkoxy, $(C_1-C_3)$haloalkyl, $(C_1-C_3)$haloalkoxy or [$(C_1-C_2)$alkoxy]-$(C_1-C_2)$alkyl and the other radical Y or X is $(C_1-C_3)$alkyl, $(C_1-C_3)$alkoxy or $(C_1-C_3)$alkylthio, each of the last-mentioned 3 radicals being unsubstituted or mono- or poly-substituted by halogen or mono- or disubstituted by $(C_1-C_3)$alkoxy or $(C_1-C_3)$alkylthio, or is halogen or a radical of the formula $NR^5R^6$, in which $R^5$ and $R^6$ independently of one another are H, $(C_1-C_3)$ alkyl or $(C_3-C_4)$alkenyl, or $(C_3-C_6)$cycloalkyl, $(C_2-C_4)$alkenyl, $(C_2-C_4)$alkynyl, $(C_3-C_4)$alkenyloxy or $(C_3-C_4)$alkynyloxy.

5. A process for the preparation of a compound of the formula (I) of claim 1 or a salt thereof, which comprises a) reacting a compound of the formula (II),

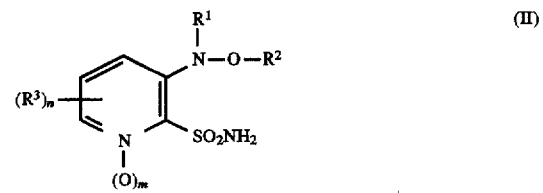 (II)

with a heterocyclic carbamate of the formula (III),

 (III)

$R^o$—O—CO—$NR^4$—A in which $R^o$ is optionally substituted phenyl or $(C_1-C_4)$ alkyl, or b) reacting a pyridylsulfonylcarbamate of the formula (IV),

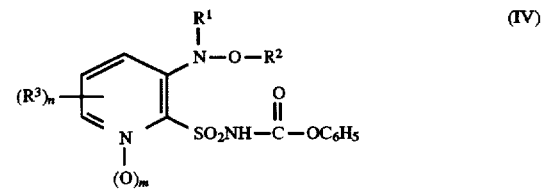 (IV)

with an amino heterocycle of the formula (V)

H—$NR^4$—A, (V)

or c) reacting a sulfonyl isocyanate of the formula (VI)

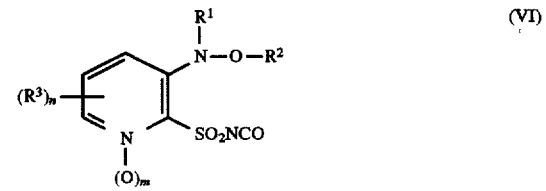 (VI)

with an amino heterocycle of the formula (V)

H—$NR^4$—A, (V)

or d) first reacting an amino heterocycle of the formula H—$NR^4$—A (V) with phosgene in a one-pot reaction in the presence of a base, and reacting the intermediate formed with a pyridinesulfonamide of the formula (II), or e) reacting a sulfonamide of the abovementioned formula (II) with a (thio)isocyanate of the formula (VII)

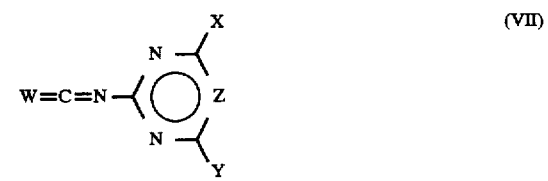 (VII)

in the presence of a base, the radicals $R^1$, $R^2$, $R^3$, $R^4$, A, W, X, Y and Z as well as m and n in the formulae (II)–(VII) being as defined in formula (I).

6. A herbicidal or plant growth-regulating composition, which comprises at least one compound of the formula (I) or a salt thereof as claimed in claim 1 and formulation auxiliaries conventionally used in crop protection.

7. A method of controlling harmful plants or of regulating the growth of plants, which comprises applying an effective amount of at least one compound of the formula (I) or a salt thereof as claimed in claim 1 to the harmful plants or to plants, the seeds of these plants or the area on which these plants grow.

8. A compound of the formula (II)

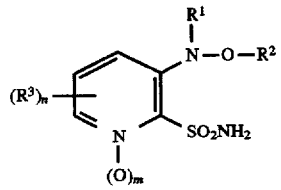
(II)

in which $R^1$, $R^2$, $R^3$, n and m are as defined in formula (I) as claimed in claim 1.

9. A compound of the formula (VIII)

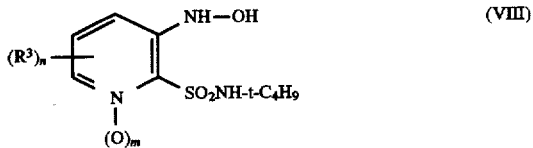
(VIII)

in which $R^1$, $R^2$, $R^3$, n and m are as defined in formula (I) as claimed in claim 1.

* * * * *